United States Patent
Rausch-Derra et al.

(10) Patent No.: US 12,109,218 B2
(45) Date of Patent: *Oct. 8, 2024

(54) COMPOSITIONS OF GRAPIPRANT AND METHODS FOR USING THE SAME

(71) Applicant: ARATANA THERAPEUTICS, INC., Leawood, KS (US)

(72) Inventors: Lesley Rausch-Derra, Parkville, MO (US); Tamara Newbold, Martinsville, NJ (US); Gopinath Devaraj, Auckland (NZ); Akemi Shiraishi, Auckland (NZ)

(73) Assignee: ARATANA THERAPEUTICS, INC., Leawood, KS (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/548,755

(22) Filed: Dec. 13, 2021

(65) Prior Publication Data

US 2022/0096501 A1   Mar. 31, 2022

Related U.S. Application Data

(60) Continuation of application No. 15/144,609, filed on May 2, 2016, now abandoned, which is a division of application No. 14/639,898, filed on Mar. 5, 2015, now Pat. No. 11,369,621.

(60) Provisional application No. 62/089,713, filed on Dec. 9, 2014.

(51) Int. Cl.
| | |
|---|---|
| *A61K 31/64* | (2006.01) |
| *A61K 9/00* | (2006.01) |
| *A61K 9/20* | (2006.01) |
| *A61K 31/437* | (2006.01) |

(52) U.S. Cl.
CPC ............ *A61K 31/64* (2013.01); *A61K 9/0053* (2013.01); *A61K 9/2009* (2013.01); *A61K 9/2013* (2013.01); *A61K 9/2018* (2013.01); *A61K 9/2027* (2013.01); *A61K 9/2054* (2013.01); *A61K 9/2059* (2013.01); *A61K 31/437* (2013.01)

(58) Field of Classification Search
CPC .... A61K 31/437; A61K 31/64; A61K 9/0053; A61K 9/0056; A61K 9/2009; A61K 9/2013; A61K 9/2018; A61K 9/2027; A61K 9/2054; A61K 9/2059; A61P 29/00
See application file for complete search history.

(56) References Cited

U.S. PATENT DOCUMENTS

| | | | |
|---|---|---|---|
| 6,710,054 | B2 | 3/2004 | Nakao et al. |
| 6,861,441 | B1 | 3/2005 | Clayton et al. |
| 7,141,580 | B2 | 11/2006 | Nakao et al. |
| 7,479,564 | B2 | 1/2009 | Nakao et al. |
| 7,960,407 | B2 | 6/2011 | Haruta et al. |
| 9,265,756 | B2 | 2/2016 | Newbold et al. |
| 11,369,621 | B2 * | 6/2022 | Rausch-Derra ...... A61K 9/2054 |
| 2002/0107273 | A1 | 8/2002 | Nakao et al. |
| 2003/0236260 | A1 | 12/2003 | Shimojo et al. |
| 2008/0206309 | A1 | 8/2008 | Jabbour et al. |
| 2008/0242713 | A1 | 10/2008 | Guilford et al. |
| 2009/0018158 | A1 | 1/2009 | Haruta et al. |
| 2009/0036495 | A1 | 2/2009 | Audoly |
| 2009/0253756 | A1 | 10/2009 | Boyd et al. |
| 2013/0225609 | A1 | 8/2013 | Nickolaus |
| 2015/0250774 | A1 | 9/2015 | Newbold et al. |

FOREIGN PATENT DOCUMENTS

| | | |
|---|---|---|
| CN | 1477960 A | 2/2004 |
| CN | 101137656 A | 3/2008 |
| CN | 101967146 A | 2/2011 |
| JP | 2006249089 A | 9/2006 |
| WO | WO-9850033 A1 | 11/1998 |
| WO | WO-0232422 A2 | 4/2002 |
| WO | 0308637 A2 | 10/2003 |
| WO | WO-2006095268 A1 | 9/2006 |
| WO | 2011102149 A1 | 8/2011 |
| WO | WO-2012048854 A2 | 4/2012 |
| WO | WO-2012048854 A3 | 6/2012 |
| WO | WO-2012122279 A1 | 9/2012 |
| WO | WO-2012157288 A1 | 11/2012 |
| WO | WO-2013017928 A1 | 2/2013 |
| WO | 2014148053 A1 | 9/2014 |

OTHER PUBLICATIONS

Antonova, Met al.. "The pharmacological effect of BGC20-1531, a novel prostanoid EP4 receptor antagonist, in the Prostaglandin E2 human model of headache," J Headache Pain, 12, pp. 551-559, 2011.
Chinese Office Action mailed Dec. 27, 2017 for corresponding Chinese Patent Application No. 201580006168.6.
European Search report mailed Sep. 22, 2017 for corresponding European Application No. 15758877.3.
Final Office Action, related to U.S. Appl. No. 14/639,898 dated Feb. 7, 2017, 13 pages.
Goodman & Gilman's The Pharmacological Basis of Therapeutics, Tenth Edition (2001). Appendix II, pp. 1917-1923, McGraw Hill Medical Publishing Division, USA.
International Search Report and the Written Opinion of the International Searching Authority, or the Declaration, PCT/US2015/019037, mailing date Jun. 8, 2015.

(Continued)

*Primary Examiner* — Kara R McMillian
(74) *Attorney, Agent, or Firm* — McBee Moore & Vanik, IP, LLC

(57) ABSTRACT

The present disclosure provides a method for treating pain or inflammation in a non-human animal in need thereof. The method comprises administering to a non-human animal a pharmaceutical composition comprising a therapeutically effective amount of grapiprant. Also provided herein are pharmaceutical compositions for treating pain or inflammation in a non-human animal in need thereof. The pharmaceutical compositions comprise a therapeutically effective amount of grapiprant and an excipient, including flavorants.

14 Claims, 11 Drawing Sheets

(56) References Cited

OTHER PUBLICATIONS

Japanese Office Action mailed Oct. 17, 2017 for corresponding Japanese Patent Application No. 2016-573691.
Johnston, Spencer A., "Osteoarthritis: Joint Anatomy, Physiology, and Pathobiology", Vet Clin North Am Small Anim Pract. ;27(4), Jul. 1997, pp. 699-723.
Murase, A., "Effect of prostanoid EP4 receptor antagonist, CJ-042,794, in rat models of pain and inflammation". Eur J Pharmacol. Feb. 2, 2008; N 580(1-2), c. 116-21, PMID:18031725.
Nakao, K et al., "CJ-023,423, a Novel, Potent and Selective Prostaglandin EP4 Receptor Antagonist with Antihyperalgesic Properties," JPET 322(2), pp. 686-694, 2007.
Office Action, related to U.S. Appl. No. 14/639,898 dated Aug. 2, 2016, 14 pages.
PR Newswire, "Aratana, Elanco Announce Global Strategic Collaboration", http://www.prnewswire.com/news-releases/aratana-elanco-announce-global-strategic-collaboration-300256859.html, Apr. 25, 2016.
PR Newswire, "Galliprant (grapiprant tablets) Now Available for Canine Osteoarthritis", http://www.prnewswire.com/news-releases/galliprant-grapiprant-tablets-now-available-for-canine-osteoarthritis-300396003.html, Jan. 24, 2017.
Rausch-Derra, Lesley C. et al, "Evaluation of the safety of long-term, daily oral administration of grapiprant, a novel drug for treatment of osteoarthritic pain and inflammation, in healthy dogs", American Journal of Veterinary Research, vol. 76, No. 10, Oct. 2015, pp. 853-859.
Roush, James K. et al., "Multicenter veterinary practice assessment of the effects of omega-3 fatty acids on osteoarthritis in dogs", Journal of the American Veterinary Medical Association, vol. 236, No. 1, Jan. 1, 2010, pp. 59-66.
Search Report issued Apr. 8, 2018 and English translation from Gorodissky and Partners for corresponding RU Application No. 2016137926.
Shaw, Kristin Kirby et al., "Grapiprant: an EP4 prostaglandin receptor antagonist and novel therapy for pain and inflammation", Veterinary Medicine and Science (2016). 10.1002/vms3.13 pp. 3-9.
"A Study of The Effect of CJ-023,423 on The Incidence of Stomach Ulcers", ClinicalTrials.gov, Identifier: NCT00392080, clinicaltrials.gov/ct2/show/NCT00392080, first posted Oct. 25, 2006.
Okumura, T. et al., "Effects of the selective EP4 antagonist, CJ-023,423 on chronic inflammation and bone destruction in rat adjuvant-induced arthritis", Journal of Pharmacy and Pharmacology, vol. 60, pp. 723-730.
Form 8-K, filing date Jan. 16, 2014, SEC Accession No. 0001193125-14-013272, Aratana Therapeutics, Inc., CIK:0001509190.
Notice of Opposition on European Patent Application 15758877.3, dated Sep. 28, 2022—KRKA Opposition.
Notice of Opposition on European Patent Application 15758877.3, dated Oct. 28, 2022, VIRBAC Opposition, machine translation of Opposition.
Communication of Notices of Opposition (R.79.91) EPC) on European Patent Application 15758877.3, dated Aug. 11, 2022.
Response to Oppositions on European Patent Application 15758877.3, filed Mar. 17, 2023.
L. Rausch-Derra et al., "Safety of the EP4 Receptor Antagonist, Grapiprant, Administered Daily to Beagle Dogs for 9 Months at 1,6 and 50 mg/kg", presented at ACVIM, Nashville, TN—Jun. 2014.
J Vet Intern Med 2014, 28, 976-1134, 2014 ACVIM Forum Research Abstracts Program, published online 2014.
K. Nakao, "CJ-023,423, a Novel, Potent and Selective Prostaglandin EP4 Receptor Antagonist with Antihyperalgesic Properties", JPET 322: pp. 686-694, 2007.
C. K. Cassel et al., "Geriatric Medicine: An Evidence-Based Approach", Springer 2003, pp. 71-75.
J. K. Aronson, "Meyler's Side Effects of Analgesics and Anti-inflammatory Drugs", Elsevier B. V. 2010, pp. 237-239.
R. S. Sinatra et al., "The Essence of Analgesia and Analgesics", Cambridge University Press 2011, pp. 66-70.
WHO Drug Information, vol. 27, No. 4, 2013, Proposed INN: List 110, pp. 399-458.
The Wayback Machine, www.aratana.investorroom.com, archive date Jan. 18, 2014 (printed version followed by screenshots).
Press Release Aratana Therapeutics Announces Positive Top-Line Results from AT-001 Dose-Ranging Field Study in Client-Owned Dogs with Osteoarthritis, provided by Aratana Therapeutics, Inc., Nov. 20, 2013.
Press Release Why Aratana Therapeutics Inc. Shares Jumped, Dec. 23, 2013.
M. Boriello et al., "Prostaglandin EP4 antagonists", Pharm. Pat. Analyst (2013) 2(3), pp. 387-397.
S. F. Crowley et al., "Aratana Therapeutics, Inc., Alpha Select List", Institutional Research, Craig-Hallum Capital Group LLC 2013, pp. 1-17.
G. Sinha, "Companion therapeutics", Nature Biotechnology, vol. 6, No. 3, Jan. 2014, pp. 12-14.
S. A. Khan et al., "Toxicology of Frequently Encountered Nonsteroidal Anti-Inflammatory Drugs in Dogs and Cats", Vet Clin Small Anim 42 (2012) pp. 289-306.
B. D. X. Lascelles, "Guidelines for Safe and Effective Use of NSAIDs in Dogs", Veterinary Therapeutics, vol. 6, No. 3, Fall 2005, pp. 237-251.
M. G. Papich, "An Update on Nonsteroidal Anti-Inflammatory Drugs (NSAIDs) in Small Animals", Vet Clin Small Anim 38 (2008) pp. 1243-1266.
Dugdale et al., "Veterinary Anaesthesia: Principles to Practice", Blackwell Publishing Ltd. 2010, pp. 19-24.
M. Kahn et al., "The Merck/Merial Manual for Pet Health", Merck & Co., Inc. 2007, p. 1140.
D. F. Woodward, "International Union of Basic and Clinical Pharmacology. LXXXIII: Classification of Prostanoid Receptors, Updating 15 Years of Progress", Pharmacol Rev 63: pp. 471-538, 2011.
V. Konya et al., "E-type prostanoid receptor 4 (EP4) in disease and therapy", Pharmacology & Therapeutics, 138 (2013), pp. 485-502.
Clinicaltrials.gov, NCT00392080, Mar. 18, 2008.
RaQualia innovators for life, 2012, http://www.raqualia.co.jp—machine translation.
R. Schmidt, "Dose-Finding Studies in Clinical Drug Development", Eur J Clin Pharmacol (1988) 34:15-19.
D. M. Boothe, Veterinary Compounding in Small Animals: A Clinical Pharmacologist's Perspective, Vet Clin Small Anim 36 (2006) pp. 1129-1173.
N. Ting et al., Dose Finding in Drug Development, Springer Science+Business Media, Inc.2006, pp. 18-29.
V. Sharma et al., "To scale or not to scale: the principles of dose extrapolation", British Journal of Pharmacology (2009), 157, pp. 907-921.
G.E. Hardee et al., "Development and Formulation of Veterinary Dosage Forms", 2nd ed., 1998, Marcel Dekker, pp. 474-477.
Guidance for Industry, 185, 2009, Target Animal Safety for Veterinary Pharmaceutical Products, VICH GL43.
R.C. Gupta et al., Veterinary Toxicology, Basic and Clinical Principles, Elsevier In. 2012, pp. 119-120.
T. Vaughan-Scott et al., "The pathophysiology and medical management of canine osteoarthritis", Jl. S.Afr.vet.Ass. (1997) 68(1): pp. 21-25.
D. C. Plumb, "Veterinary Drug Handbook", 7th edition, PharmaVet Inc. 2011, pp. 2929-2936.
R. C. Gupta, "Veterinary Toxicology: Basic and Clinical Principals", Elsevier Inc. 2007, pp. 368-373.
H. Wen et al., "Oral Controlled Release Formulation Design and Drug Delivery", John Wiley & Sons, Inc. 2010, pp. 257-258.
J. Zheng, "Formulation and analytical development for low-dose oral drug products", John Wiley & Sons, Inc. 2009, pp. 331-333.
J. K. H. Ma et al., "Basic Physical Pharmacy", 2013 Jones & Bartlett Learning, LLC, pp. 248-252.
L. L. Augsburger et al., "Pharmaceutical Dosage Forms: Tablets", 3rd edition, Informa Healthcare, 2008, Chapter 13, pp. 383-431.
Rausch-Derra et al., "Evaluation of the safety of long-term, daily oral administration of grapiprant, a novel drug for treatment of

(56) References Cited

OTHER PUBLICATIONS osteoarthritic pain and inflammation, in heatly dogs," American Journal of Veterinary Research (AVJR), Oct. 2015, vol. 76, No. 10, pp. 853-859.
Jones et al., "Prostanoid receptor antagonists: development strategies and therapeutic applications, British Journal of Pharmacology", 2009, 158, 104-145.
Maubach et al., "BGC20-1531, a novel, otent and selective prostanoid EP4 receptor antagonist: a putative new treatment for migrain headache", British Journal of Pharmacology, 2009, 156, 316-327.
Castleberry et al., "Molecular cloning and functional characterization of the canine prostaglandin E2, receptor EP4 subtype", Prostaglandins & other Lipid Mediators, 2001, vol. 65, pp. 167-187.
Papich Handbook of Veterinary Drugs, Fifth Edition, Elsevier, Mar. 30, 2020, 13 first pages presentation pages and pp. 418-420 only.
I. Sartini et al., "Grapiprant: A Snapshot of the current knowledge", Journal of Veterinary Pharmacology and Therapeutics, 2021, published online May 31, 2021.
Heather K. Knych et al., "Detection and pharmacokinetics of grapiprant following oral administration to exercised Thoroughbred horses", Drug Test Anal., 2018, vol. 10, pp. 1237-1243, published online Mar. 25, 2018.
A. Nagahisa & T. Okumura, "Pharmacology of grapiprant, a novel EP4 antagonist: receptor binding, efficacy in a rodent postoperative pain model, and a dose estimation for controlling pain in dogs", J. vet. Pharmacol. Therap., 2016, 40, pp. 285-292, published online Sep. 6, 2016.
S. Cox et al., "Determination of grapiprant plasma and urine concentrations in horses", Veterinary Anaesthesia and Analgesia, 2020, vol. 47, pp. 705-709, published online Mar. 25, 2018.
Communication de Aratana Therapeutics, published on Jan. 19, 2015, www.prnewswire.com/news-releases/aratana-therapeutics-awarded-best-pipeline-2014-byanimal-pharm-300022144.html.
Communication from Aratana Therapeutics, published on May 2, 2014 regarding their attendance at the ACVIM 2014 conference scheduled for Jun. 4-7, 2014 in Nashville, Tennessee for three oral presentations and three poster presentations; aratana.investorroom.com/2014-05-02-Aratana-Therapeutics-to-Present-at-2014-ACVIM-Forum.
Communication from Aratana Therapeutics, published on Jun. 9, 2014 and relating to their attendance at the ACVIM 2014 conference which took place on Jun. 4-7, 2014 in Nashville, Tennessee, describing a summary of the three oral presentations and three poster presentations; aratana.investorroom.com/2014-06-09-Aratana-Therapeutics-Presents-Safety-and-Clinical-Findings-at-2014-ACVIM-Forum.
"VICH Topic GL9 (GCP)—Step 7 Consensus Guideline", Guideline on Good Clinical Practices, CVMP/VICH/595/98—Final, The European Agency for the Evaluation of Medicinal Products, Veterinary Medicines and information Technology Unit, London, Jul. 4, 2000.
"A Placebo-Controlled, Dose Ranging, Field Study to Evaluate the Safety and Effectiveness of AT-001, Administered Daily as an Oral Tablet, for the Control of Pain and Inflammation Associated With Osteoarthritis in Dogs", Protocol No. AT001-CCL-12-004, Aratana Therapeutics, Inc., Dec. 10, 2012, pp. 1-28.
Amendment No. 5 to Form S-1 Registration Statement under the securities act of 1933, Aratana Therapeutics, Inc., Registration No. 333-187372.
"CVMP assessment report for Galliprant (EMEA/V/C/004222/0000)—International non-proprietary name: grapiprant", Committee for Medicinal Products for Veterinary Use, Nov. 9, 2017, European Medicines Agency, Science Medicines Health, EMA/747932/2017, Veterinary Medicines Division.
"The Committee for Veterinary Medicinal Products (CVMP) is the European Medicines Agency's (EMA) committee responsible for veterinary medicines.", Committee for Veterinary Medicinal Products (CVMP).
Cunningham et al., "Interspecies Allometric Scaling", Comparative and Veterinary Pharmacology, Springer Heidelberg Dordrecht, pp. 149-152, DOI 10.2007/978-3-642-10324-7.
Murase, Akio, et al. "Characterization of Binding Affinity of CJ-023,423 for Human Prostanoid EP4 Receptor" Pharmacology, vol. 82, No. 1, pp. 10-14, Apr. 11, 2008.

* cited by examiner

COMPOSITIONS OF GRAPIPRANT AND METHODS FOR USING THE SAME

CROSS-REFERENCE

This present application is continuation of U.S. application Ser. No. 15/144,609 filed May 2, 2016, and entitled "Compositions of Grapiprant and Methods for Using the Same" which, is a divisional of U.S. application Ser. No. 14/639,898 filed Mar. 5, 2015, and entitled "Compositions of Grapiprant and Methods for Using the Same," which claims priority to U.S. provisional application Ser. No. 62/089,713 filed Dec. 9, 2014, and entitled "Compositions of Grapiprant and Methods for Using the Same," the entire disclosures of which are incorporated herein by reference.

TECHNICAL FIELD

The present disclosure generally relates to compositions of grapiprant and methods for using the same.

BACKGROUND

Grapiprant is a prostaglandin E2 subtype 4 ($EP_4$) receptor antagonist useful in treating pain and inflammation. Formulations of grapiprant are valuable because they alter the pharmacokinetic properties of the drug within an organism, such as the peak plasma concentration, time achieved, the half-life, and the area under the plasma concentration curve ($C_{max}$, $T_{max}$, $t_{1/2}$, and AUC, respectively). Another consideration while formulating a pharmaceutical composition is the palatability of the dosage form, which improves the animal's compliance in taking the medicine.

SUMMARY

Briefly, therefore, one aspect of the present disclosure encompasses a method for treating pain or inflammation in a non-human animal in need thereof. The method comprises administering to a non-human animal a pharmaceutical composition comprising a therapeutically effective amount of grapiprant. The pharmaceutical composition may be administered orally. The administering may achieve a $C_{max}$ of grapiprant of about 375 ng/mL to about 10000 ng/mL at a $T_{max}$ of about 0.4 to about 3.4 hours, such as $C_{max}$ of grapiprant of 750 about ng/mL to about 4000 ng/mL, or of about 1300 ng/mL to about 4000 ng/mL. The $C_{max}$ of grapiprant may also be achieved at a $T_{max}$ of about 0.7 to about 1.7 hours, such as a $T_{max}$ of about 0.5 to about 1.0 hours. The grapiprant is administered at a dosage rate of about 1 to about 10 mg per kilogram bodyweight of the non-human animal per day (mg/kg/day), more specifically a dosage rate of about 2 to about 4 mg/kg/day. The pharmaceutical composition may be administered at least once daily, or at least twice daily, such as at least thrice daily. The pharmaceutical composition may be administered until the cause of pain subsides, for example from about 6 days to about 9 months. The non-human animal may be a companion animal, such as a dog, cat, or horse. In exemplary embodiments, the pharmaceutical formulation may be administered twice daily at a dosage of about 2 to about 4 mg/kg/day for about 9 to about 21 days, and the administering may achieve a $C_{max}$ of grapiprant of about 750 ng/mL to about 2200 ng/mL at a $T_{max}$ of about 0.7 to about 1.7 hours. In other embodiments, the pharmaceutical formulation may be administered to the non-human animal at about 10 to about 18 hours before surgery.

Another aspect of the disclosure provides a pharmaceutical composition for treating pain or inflammation in a non-human animal in need thereof. The pharmaceutical composition comprises a therapeutically effective amount of grapiprant and an excipient. The excipient may comprise one or more selected from the group consisting of lactose, sodium starch glycolate, microcrystalline cellulose, colloidal silicon dioxide, magnesium stearate, copovidone, and poloxamer. In particular embodiments, the pharmaceutical composition may comprise about 5% to about 15% grapiprant (w/w of the total composition), about 20% to about 80% lactose (w/w of the total composition), about 15% to about 80% microcrystalline cellulose (w/w of the total composition), about 1% to about 10% sodium starch glycolate (w/w of the total composition), about 1% to about 10% copovidone (w/w of the total composition), about 0.5% to about 3% magnesium stearate (w/w of the total composition), about 0.5% to about 4% poloxamer (w/w of the total composition), and about 0.1% to about 1% colloidal silicon dioxide (w/w of the total composition). The pharmaceutical may further comprise about 1% to about 30% flavorant (w/w of the total composition), such as about 5% to about 15% flavorant (w/w of the total composition).

The disclosure also provides a method for treating pain or inflammation in a non-human animal in need thereof, comprising orally administering to the non-human animal a pharmaceutical composition comprising a therapeutically effective amount of grapiprant; wherein the administering achieves a $C_{max}$ of grapiprant of 675 ng/mL to 5000 ng/mL within 4 hours after administration and a half-life of less than 14 hours. The $C_{max}$ may be achieved within 1 hour after administration. The pharmaceutical formulation may be administered once daily at a dosage rate of 3 mg/kg/day to 15 mg/kg/day for 28 days, for example at a rate of 3 mg/kg/day, 9 mg/kg/day, or 15 mg/kg/day.

Additional embodiments and features are set forth in part in the description that follows, and in part will become apparent to those skilled in the art upon examination of the specification, or may be learned by the practice of the embodiments discussed herein. A further understanding of the nature and advantages of certain embodiments may be realized by reference to the remaining portions of the specification the drawings, the chemical structures, and descriptions, which forms a part of this disclosure.

BRIEF DESCRIPTION OF DRAWINGS

In addition to the exemplary aspects and embodiments described above, further aspects and embodiments will become apparent by reference to the drawings and by study of the following descriptions.

DETAILED DESCRIPTION

Figure 1:
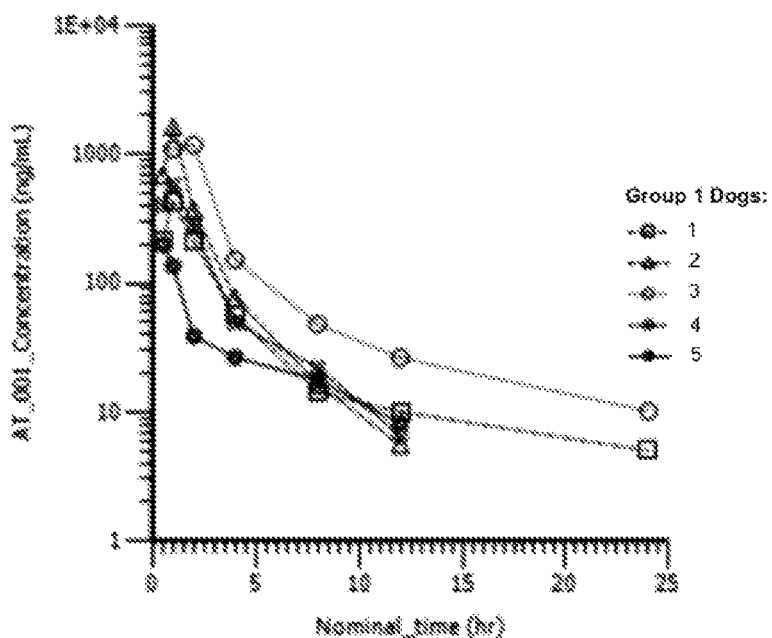
FIG. 1 depicts individual serum concentrations of grapiprant over time for Group 1 dogs, as described in Example 3.
Figure 2:
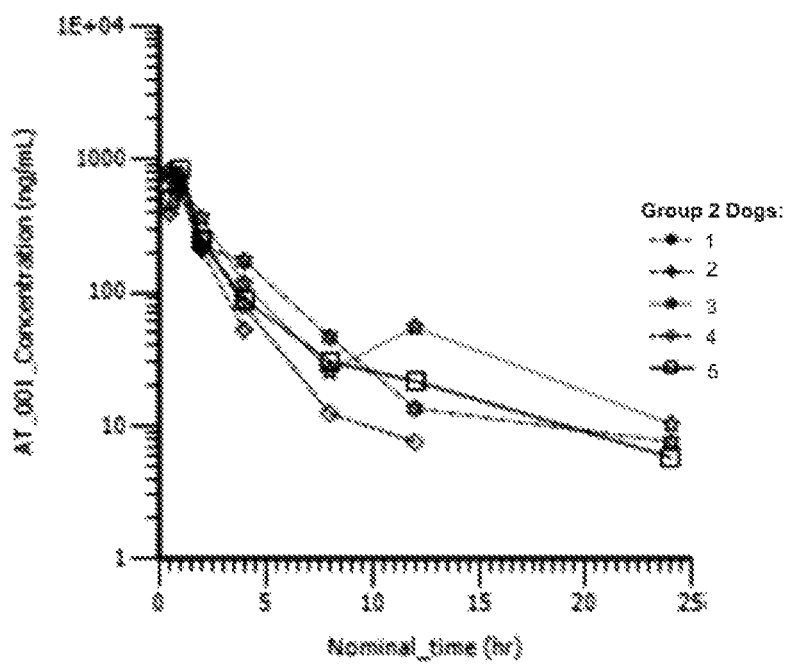
FIG. 2 depicts individual serum concentrations of grapiprant over time for Group 2 dogs, as described in Example 3.
Figure 3:
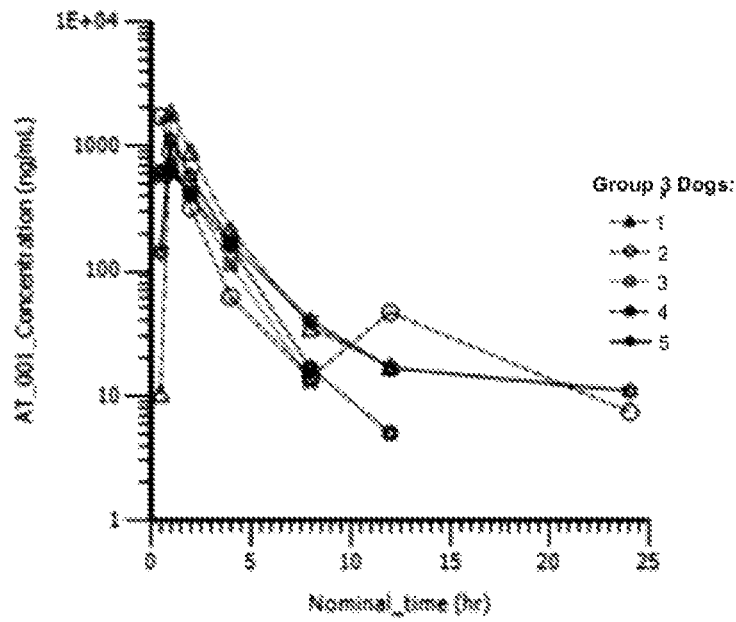
FIG. 3 depicts individual serum concentrations of grapiprant over time for Group 3 dogs, as described in Example 3.
Figure 4:
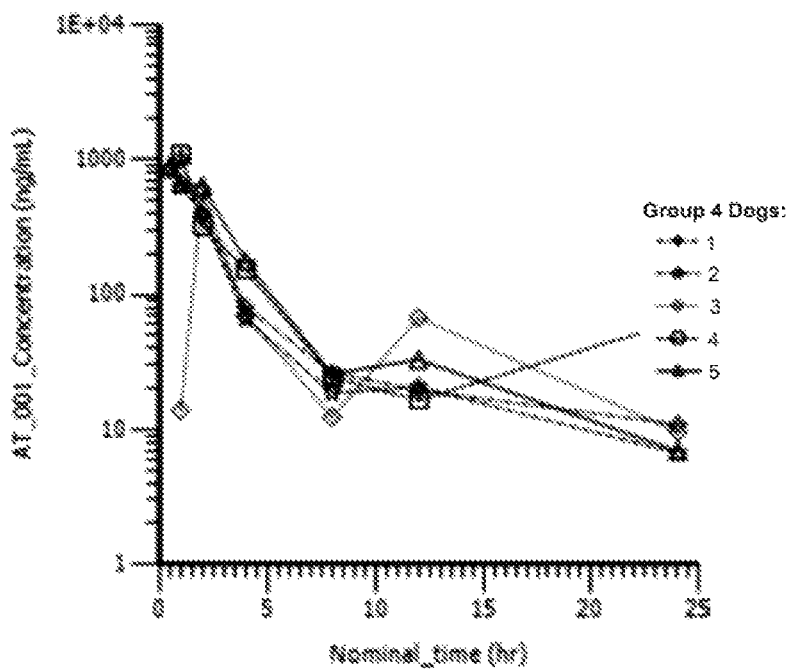
FIG. 4 depicts individual serum concentrations of grapiprant over time for Group 4 dogs, as described in Example 3.
Figure 5:
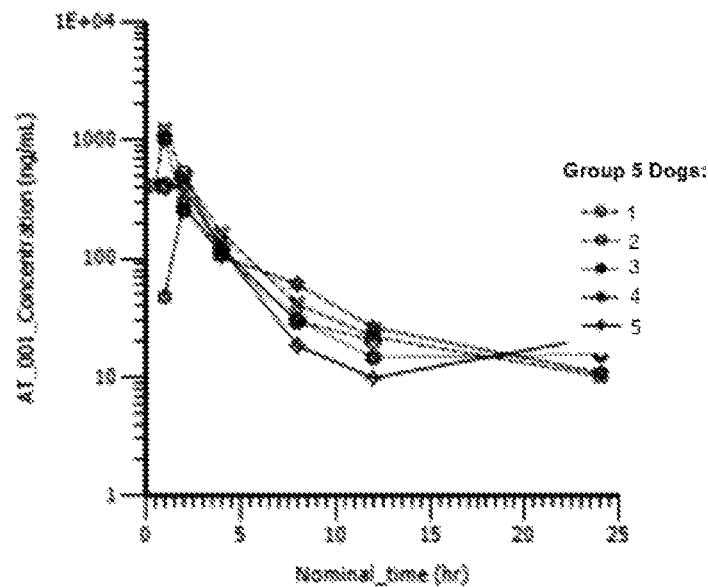
FIG. 5 depicts individual serum concentrations of grapiprant over time for Group 5 dogs, as described in Example 3.
Figure 6:
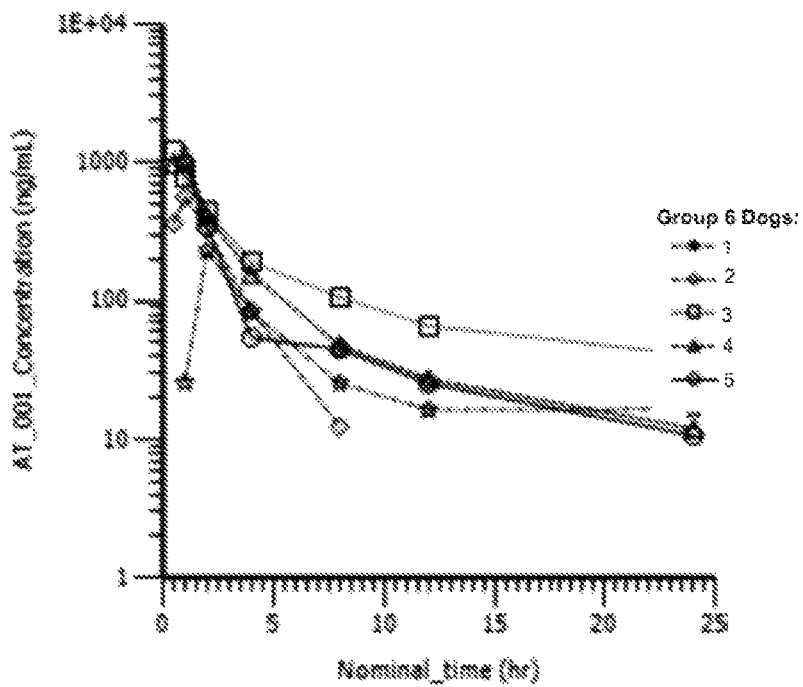
FIG. 6 depicts individual serum concentrations of grapiprant over time for Group 6 dogs as described in Example 3.

Grapiprant is a prostaglandin E2 subtype 4 (EP$_4$) receptor antagonist. Grapiprant has a CAS registry number of 415903-37-6 and is also referred to variously as AT-001, CJ-023,423, RQ-7, RQ-00000007, MR10A7, AAT-007, N-{2-[4-(2-ethyl-4,6-dimethyl-1H-imidazo[4,5-c]pyridin-1-yl)phenyl]ethyl}-N'-[(4-methylphenyl)sulfonyl]urea, N-[[[2-[4-(2-ethyl-4,6-dimethyl-1H-imidazo[4,5-c]pyridin-1-yl)phenyl]ethyl]amino] carbonyl]-4-methyl-benenesulfonamide, or 2-ethyl-4,6-dimethyl-3-(4(2-(((((4-methylphenyl)sulfonyl)amino) carbonyl) amino)ethyl)phenyl)-3H-imidazo[4,5-c]pyridine. The chemical structure and synthesis of grapiprant are described in WO 2002/032900 and U.S. Pat. Nos. 6,710,054, 7,141,580, and 7,479,564, the disclosures of which are all included herein by reference in their entireties. Grapiprant has the following chemical structure:

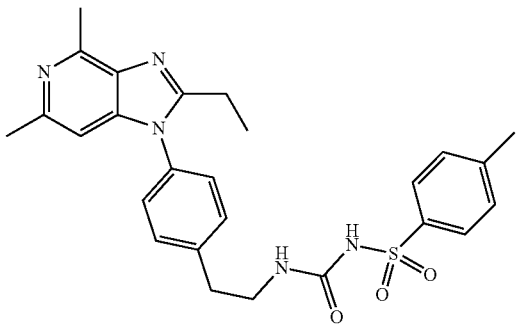

Without wishing to be bound by theory, prostaglandin E2 (PGE2) is a potent modulator involved in the pathogenesis of a variety of diseases such as inflammation, pain, arthritis, and cancer. PGE2 binds to at least four subtypes of PGE receptor, designated EP$_1$, EP$_2$, EP$_3$, and EP$_4$. Molecular pharmacology studies have revealed that all subtypes are 7-transmembrane spanning receptors that belong to the G-protein coupled receptor super family. EP$_1$ activation stimulates the release of intracellular calcium; EP$_2$ and EP$_4$ stimulation both activate adenylate cyclase but differ in their response to certain ligands; and EP$_3$ stimulation inhibits adenylate cyclase via inhibitory G-proteins.

In vivo, grapiprant inhibits [$^3$H]PGE binding to human, rat, and dog EP$_4$ receptors with a K$_i$ of 13±4 nM, 20±1 nM, and 24.1±2.7 nM respectively. Grapiprant is highly selective for the EP$_4$ receptor over other human prostanoid receptor subtypes and inhibits PGE$_2$-evoked elevation in intracellular cAMP at the human and rat EP$_4$ receptors with pA2 of 8.3±0.03 and 8.2±0.2 nM, respectively. Oral administration of grapiprant significantly reduces thermal hyperalgesia induced by intraplantar injection of PGE$_2$ (ED$_{50}$=12.8 mg/kg). Grapiprant is effective in models of acute and chronic inflammatory pain. Grapiprant significantly reduces mechanical hyperalgesia induced by carrageenan model and reverses complete Freund's adjuvant-induced chronic inflammatory pain response. Taken together, grapiprant is a potent and selective antagonist of human and rat EP$_4$ receptors, produces antihyperalgesic effects in animal models of inflammatory pain.

Grapiprant may exist as any of several polymorphs. The polymorphs differ from each other with respect to their physical properties, spectral data, stability, and methods of preparation. Some crystalline forms have already been described, for example Form A, Form B, Form C, Form D, and Form G as described in U.S. Pat. No. 7,960,407, ethyl acetate solvate Form I and Form II as described in WO 2012/157288, and From X, Form X2, Form X3, and Form B4 as described in co-pending application entitled "Crystalline Forms of Grapiprant," the disclosures of which are incorporated by reference in their entireties.

(I) Pharmaceutical Compositions

One aspect of the disclosure provides for a pharmaceutical composition for treating pain or inflammation in a non-human animal in need thereof, comprising a therapeutically effective amount of grapiprant and an excipient.

Grapiprant may be included within the composition in one or more concentrations. In general, the concentration of grapiprant may range from about 1% to about 30% (w/w) of the total composition; that is, the amount of grapiprant may be from about 1% to about 30% by weight in relation to all components in the pharmaceutical composition, including the grapiprant and excipients. In various embodiments, the concentration of grapiprant may be from about 1% to about 2%, from about 2% to about 3%, from about 3% to about 4%, from about 4% to about 5%, from about 5% to about 6%, from about 6% to about 7%, from about 7% to about 8%, from about 8% to about 9%, from about 9% to about 10%, from about 10% to about 11%, from about 11% to about 12%, from about 12% to about 13%, from about 13% to about 14%, from about 14% to about 15%, from about 15% to about 16%, from about 16% to about 17%, from about 17% to about 18%, from about 18% to about 19%, from about 19% to about 20%, from about 20% to about 21%, from about 21% to about 22%, from about 22% to about 23%, from about 23% to about 24%, from about 24% to about 25%, from about 25% to about 26%, from about 26% to about 27%, from about 27% to about 28%, from about 28% to about 29%, or from about 29% to about 30% (w/w) of the total composition.

In exemplary embodiments, the concentration of grapiprant may be from about 5% to about 15% (w/w) of the total composition. In one embodiment, the concentration of grapiprant may less than about 30% (w/w) of the total composition. In another embodiment, the concentration of grapiprant may be more than about 1% (w/w) of the total composition.

In some embodiments, grapiprant may be provided in a pharmaceutical composition at a concentration suitable to alleviate the pain or inflammation in a non-human animal. The grapiprant may be provided at a concentration suitable to alleviate pain or inflammation in the non-human animal in need thereof for about 6 days, for about 7 days, for about 8 days, for about 9 days, for about 10 days, for about 11 days, for about 12 days, for about 13 days, for about 14 days, for about 15 days, for about 16 days, for about 17 days, for about 18 days, for about 19 days, for about 20 days, for about 21 days, for about 22 days, for about 23 days, for about 24 days, for about 25 days, for about 26 days, for about 27 days, or for about 28 days.

In exemplary embodiments, the grapiprant may be provided at a concentration suitable to alleviate pain or inflammation in the non-human animal in need thereof for about 9 days to about 21 days. In other exemplary embodiments, the grapiprant may be provided at a concentration suitable to alleviate pain or inflammation in the non-human animal in need thereof for about 12 days to about 14 days. In some embodiments, the grapiprant may be provided at a concentration suitable to alleviate pain or inflammation in the non-human animal in need thereof for about 1 month, about 2 months, about 3 months, about 4 months, about 5 months, about 6 months, about 7 months, about 8 months, or about 9 months, or longer. In one embodiment, the grapiprant may be provided at a concentration suitable to alleviate pain or inflammation in the non-human animal in need thereof for less than about 28 days. In another embodiment, the grapiprant may be provided at a concentration suitable to alleviate pain or inflammation in the non-human animal in need thereof for at least about 9 days.

In other embodiments, grapiprant may be at least partially dissolved in an aqueous solvent (e.g., deionized and/or purified water). In some other embodiments, the grapiprant may be formulated as a suspension. The concentration of grapiprant within the composition may be at least partially dependent upon the route of administration and/or the number of times in a pre-determined time period the composition is administered to a non-human animal. For example, one or more compositions may be designed for injectable administration. As a result, the grapiprant within the composition may be delivered directly to the circulatory system (e.g., via intravenous administration), thereby circumventing the need for absorption in the alimentary canal. Accordingly, greater amounts of grapiprant may reach the desired targets relative to oral formulations, leading to a lower necessary concentration of grapiprant in a sterile injectable version.

In other embodiments, the pharmaceutical composition may be orally administered one or more times per day, such as at least twice daily or at least thrice daily. For example, the pharmaceutical composition may be administered as a solution, a suspension, a solid, or a viscous liquid formulation. Correspondingly, the greater number of times per day the composition is administered to the non-human animal, a lesser the amount of grapiprant may produce the target result. In exemplary embodiments, the pharmaceutical composition may be formulated for oral administration, such as an oral solution or an oral suspension or an oral gel.

A variety of excipients commonly used in pharmaceutical formulations may be selected on the basis of several criteria such as, for example, the desired dosage form and the release profile properties of the dosage form. Non-limiting examples of suitable excipients include an agent selected from the group comprising a binder, a filler, a non-effervescent disintegrant, an effervescent disintegrant, a preservative, a diluent, a flavoring agent, a sweetener, a lubricant, an oral dispersing agent, a coloring agent, a taste masking agent, a pH modifier, a stabilizer, a compaction agent, and combinations of any of these agents.

In one embodiment, the excipient may be a binder, which holds the pharmaceutical composition together until administration. Suitable binders include starches, pregelatinized starches, gelatin, polyvinylpyrrolidone, cellulose, methylcellulose, sodium carboxymethyl cellulose, ethylcellulose, polyacrylamides, polyvinyloxoazolidone, polyvinyl alcohols, $C_{12}$-$C_{18}$ fatty acid alcohol, polyethylene glycol, polyols, saccharides, oligosaccharides, polypeptides, peptides, and combinations thereof.

In another embodiment, the excipient may be a filler, which adds bulk to the pharmaceutical composition for easier handling and more accurate dosing. Suitable fillers include carbohydrates, inorganic compounds, and polyvinylpyrrolidone. By way of non-limiting example, the filler may be calcium sulfate, e.g. both di- and tri-basic calcium sulfate; starch, calcium carbonate, magnesium carbonate, microcrystalline cellulose, dibasic calcium phosphate, magnesium oxide, calcium silicate, talc, modified starches, lactose, sucrose, mannitol, and sorbitol.

The excipient may be a non-effervescent disintegrant, which allows the pharmaceutical composition to more easily dissolve after administration without evolving gas. Suitable examples of non-effervescent disintegrants include starches (such as corn starch, potato starch, and the like), pregelatinized and modified starches thereof, sweeteners, clays (such as bentonite), microcrystalline cellulose, alginates, sodium starch glycolate, and gums (such as agar, guar, locust bean, karaya, pecitin, and tragacanth).

In another embodiment, the excipient may be an effervescent disintegrant, which allows the pharmaceutical composition to more easily dissolve during administration while evolving gas. By way of non-limiting example, suitable effervescent disintegrants include sodium bicarbonate in combination with citric acid, and sodium bicarbonate in combination with tartaric acid.

The excipient may comprise a preservative, which increases the stability and storage lifetime of the pharmaceutical composition, particularly delaying unwanted degradation of the active ingredient. Suitable examples of preservatives include antioxidants (such as alpha-tocopherol or ascorbate) and antimicrobials (such as parabens, chlorobutanol or phenol). In other embodiments, an antioxidant such as butylated hydroxytoluene (BHT) or butylated hydroxyanisole (BHA) may be used.

The excipient may include a diluent, which diminishes the relative concentrations of other components within the pharmaceutical composition. Diluents suitable for use include pharmaceutically acceptable saccharides such as sucrose, dextrose, lactose, microcrystalline cellulose, fructose, xylitol, and sorbitol; polyhydric alcohols; starches; pre-manufactured direct compression diluents; and mixtures of any of the foregoing.

The excipient may comprise a surfactant, which alters the solubility parameters of the other components within the pharmaceutical composition. In various embodiments, the surfactant may be an alkylaryl polyether alcohol, such as Triton™ X-100, Surfonic™ N-100 (nonoxaynol-10), or Witconol™ NP-100; or a poloxamer, such as Pluronic™, Synperonic™, or Kolliphor™. Other suitable examples of surfactants include, for example, 2-acrylamido-2-methylpropane sulfonic acid, alkyl polyglycoside, ammonium perfluorononanoate, benzalkonium chloride (BAC), benzethonium chloride (BZT), 5-bromo-5-nitro-1,3-dioxane, cetyl trimethylammonium bromide (CTAB, hexadecyltrimehtylammonium bromide, cetyl trimethylammonium chloride), cetylpridinium chloride (CPC), cyclohexyl-1-hexyl-maltopyranoside, decylmaltopyranoside, decyl polyglucose, dimethyldioctadecylammonium chloride, dioctadecyldimethylammmonium bromide (DODAB), dipalmitoylphosphatidylcholine, lauryldimethylamine oxide, dodecylmaltopyranoside, magnesium laureth sulfate polyethoxylated tallow amine (POEA), octenidine dihydrochloride, octylphenoxypolyethoxyethanol (Igepal™ CA-630), octylthioglucopyranoside (OTG), ox gall, sodium nonanoyloxybenzensulfonate, sorbitan monolaurate, surfactin, and thonozonium bromide. In exemplary embodiments, the surfactant may be a poloxamer or sodium lauryl sulfate.

The excipient may be a lubricant, which allows easier removal of the pharmaceutical composition from molds during manufacture and may aid administration of the pharmaceutical composition. Suitable non-limiting examples of lubricants include magnesium stearate, calcium stearate, zinc stearate, hydrogenated vegetable oils, sterotex, polyoxyethylene monostearate, talc, polyethyleneglycol, sodium benzoate, sodium lauryl sulfate, magnesium lauryl sulfate, and light mineral oil.

The excipient may be a dispersion enhancer, which aids dispersion of the components of the pharmaceutical composition within the subject after administration. Suitable dispersants may include starch, alginic acid, polyvinylpyrrolidones, guar gum, kaolin, bentonite, purified wood cellulose, sodium starch glycolate, isomorphous silicate, and microcrystalline cellulose.

Depending upon the embodiment, it may be desirable to provide a coloring agent, which aids visualization and identification of the pharmaceutical composition. Suitable color additives include food, drug and cosmetic colors (FD&C), drug and cosmetic colors (D&C), or external drug and cosmetic colors (Ext. D&C). These colors or dyes, along with their corresponding lakes, and certain natural and derived colorants may be suitable for use in the present disclosure depending on the embodiment.

In various embodiments, the excipient may include a pH modifier, which may alter the solubility profile and bioavailability parameters of components within the pharmaceutical composition. In certain embodiments, the pH modifier may include sodium carbonate or sodium bicarbonate.

The weight fraction of the excipient or combination of excipients in the pharmaceutical composition may be about 98% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the pharmaceutical composition.

In particular embodiments, the excipient may comprise one or more selected from the group consisting of lactose, sodium starch glycolate, microcrystalline cellulose, colloidal silicon dioxide, magnesium stearate, copovidone, surfactant, poloxamer, and sodium laurel sulfate.

The concentration of lactose within the pharmaceutical composition may vary. In general, the concentration of lactose may range from about 10% to about 95% (w/w) of the total composition. In various embodiments, the concentration of lactose may be from about 10% to about 15%, from about 15% to about 20%, from about 20% to about 25%, from about 25% to about 30%, from about 30% to about 35%, from about 35% to about 40%, from about 40% to about 45%, from about 45% to about 50%, from about 50% to about 55%, from about 55% to about 60%, from about 60% to about 65%, from about 65% to about 70%, from about 70% to about 75%, from about 75% to about 80%, from about 80% to about 85%, from about 85% to about 90%, or from about 90% to about 95% (w/w) of the total composition. In exemplary embodiments, the concentration of lactose may be from about 20% to about 80% (w/w) of the total composition.

The concentration of microcrystalline cellulose within the pharmaceutical composition may vary. In general, the concentration of microcrystalline cellulose may range from about 5% to about 95% (w/w) of the total composition. In various embodiments, the concentration of microcrystalline cellulose may be from about 5% to about 10%, from about 10% to about 15%, from about 15% to about 20%, from about 20% to about 25%, from about 25% to about 30%, from about 30% to about 35%, from about 35% to about 40%, from about 40% to about 45%, from about 45% to about 50%, from about 50% to about 55%, from about 55% to about 60%, from about 60% to about 65%, from about 65% to about 70%, from about 70% to about 75%, from about 75% to about 80%, from about 80% to about 85%, from about 85% to about 90%, or from about 90% to about 95% (w/w) of the total composition. In exemplary embodiments, the concentration of microcrystalline cellulose may be from about 15% to about 80% (w/w) of the total composition.

The concentration of sodium starch glycolate within the pharmaceutical composition may vary. In general, the concentration of sodium starch glycolate may range from about 1% to about 20% (w/w) of the total composition. In various embodiments, the concentration of sodium starch glycolate may be from about 1% to about 2%, from about 2% to about 3%, from about 3% to about 4%, from about 4% to about 5%, from about 5% to about 6%, from about 6% to about 7%, from about 7% to about 8%, from about 8% to about 9%, from about 9% to about 10%, from about 10% to about 11%, from about 11% to about 12%, from about 12% to about 13%, from about 13% to about 14%, from about 14% to about 15%, from about 15% to about 16%, from about 16% to about 17%, from about 17% to about 18%, from about 18% to about 19%, or from about 19% to about 20% (w/w) of the total composition. In exemplary embodiments, the concentration of sodium starch glycolate may be from about 1% to about 10% (w/w) of the total composition.

The concentration of copovidone within the pharmaceutical composition may vary. In general, the concentration of copovidone may range from about 1% to about 20% (w/w) of the total composition. In various embodiments, the concentration of copovidone may be from about 1% to about 2%, from about 2% to about 3%, from about 3% to about 4%, from about 4% to about 5%, from about 5% to about 6%, from about 6% to about 7%, from about 7% to about 8%, from about 8% to about 9%, from about 9% to about 10%, from about 10% to about 11%, from about 11% to about 12%, from about 12% to about 13%, from about 13% to about 14%, from about 14% to about 15%, from about 15% to about 16%, from about 16% to about 17%, from about 17% to about 18%, from about 18% to about 19%, or from about 19% to about 20% (w/w) of the total composition. In exemplary embodiments, the concentration of copovidone may be from about 1% to about 10% (w/w) of the total composition.

The concentration of magnesium stearate within the pharmaceutical composition may vary. In general, the concentration of magnesium stearate may range from about 0.1% to about 5% (w/w) of the total composition. In various embodiments, the concentration of magnesium stearate may be from about 0.1% to about 0.5%, from about 0.5% to about 1%, from about 1% to about 1.5%, from about 1.5% to about 2%, from about 2% to about 2.5%, from about 2.5% to about 3%, from about 3% to about 3.5%, from about 3.5% to about 4%, from about 4% to about 4.5%, or from about 4.5% to about 5% (w/w) of the total composition. In exemplary embodiments, the concentration of magnesium stearate may be from about 0.5% to about 3% (w/w) of the total composition.

The concentration of surfactant within the pharmaceutical composition may vary. In general, the concentration of surfactant may range from about 0.1% to about 5% (w/w) of the total composition. In various embodiments, the concentration of surfactant may be from about 0.1% to about 0.5%, from about 0.5% to about 1%, from about 1% to about 1.5%, from about 1.5% to about 2%, from about 2% to about 2.5%, from about 2.5% to about 3%, from about 3% to about 3.5%, from about 3.5% to about 4%, from about 4% to about 4.5%, or from about 4.5% to about 5% (w/w) of the total composition. In exemplary embodiments, the concentration of surfactant may be from about 0.5% to about 4% (w/w) of the total composition.

The concentration of colloidal silicon dioxide within the pharmaceutical composition may vary. In general, the concentration of colloidal silicon dioxide may range from about 0.1% to about 2% (w/w) of the total composition. In various embodiments, the concentration of colloidal silicon dioxide may be from about 0.1% to about 0.2%, from about 0.2% to about 0.3%, from about 0.3% to about 0.4%, from about 0.4% to about 0.5%, from about 0.5% to about 0.6%, from about 0.6% to about 0.7%, from about 0.7% to about 0.8%, from about 0.8% to about 0.9%, from about 0.9% to about 1.0%, from about 1.0% to about 1.1%, from about 1.1% to about 1.2%, from about 1.2% to about 1.3%, from about 1.3% to about 1.4%, from about 1.4% to about 1.5%, from about 1.5% to about 1.6%, from about 1.6% to about 1.7%, from about 1.7% to about 1.8%, from about 1.8% to about 1.9%, or from about 1.9% to about 2.0% (w/w) of the total composition. In exemplary embodiments, the concentration of colloidal silicon dioxide may be from about 0.5% to about 1% (w/w) of the total composition.

In an exemplary embodiment, the pharmaceutical composition may comprise about 5% to about 15% grapiprant (w/w), about 20% to about 80% lactose (w/w), about 15% to about 80% microcrystalline cellulose (w/w), about 1% to about 10% sodium starch glycolate (w/w), about 1% to about 10% copovidone (w/w), about 0.5% to about 3% magnesium stearate (w/w), about 0.5% to about 4% surfactant (w/w), and about 0.1% to about 1% colloidal silicon dioxide (w/w).

(i) Flavorants

It may be necessary to add one or more additional compounds to the pharmaceutical composition in order to increase palatability. The excipient may include a flavorant that may act as a flavoring agent and/or as a flavor-masking agent. In some embodiments, the flavorant may comprise one or more of a sweetening agent, a savory agent (i.e., an agent that imbues the pharmaceutical composition with a salty flavor), a bittering agent, and a souring agent. Flavorants may be chosen from synthetic flavor oils and flavoring aromatics and/or natural oils, extracts from plants, leaves, flowers, fruits, and combinations thereof. By way of example, these may include cinnamon oils, oil of wintergreen, peppermint oils, clover oil, hay oil, anise oil, *eucalyptus*, vanilla, citrus oils (such as lemon oil, orange oil, grape and grapefruit oil), and fruit essences (such as apple, peach, pear, strawberry, raspberry, cherry, plum, pineapple, and apricot). In some embodiments, the flavoring agents and/or flavor-masking agents may comprise a vanilla-comprising composition, for example ethylvanillin, vanillin-RHD, vanillin-Merck, vanilla-TG-old, and suitable solvents (e.g., ethanol and/or water). In other embodiments, other flavorants may be added that confer other flavors on the composition, such as banana, pork liver, beef, etc.

In some embodiments, the flavoring agents and/or flavor-masking agents can comprise a vanilla-comprising composition, such as, but not limited to ethyl vanillin, vanillin (vanillin-RHD), natural vanilla flavor (vanillin-Merck), nature-identical vanilla flavor (vanilla-TG-old), and suitable solvents (e.g., ethanol and/or water).

In other embodiments, the flavoring agents and/or flavor-masking agents can comprise one or more selected from chicken, bacon, beef, pork, liver, fish, honey, caramel, and banana.

In another embodiment, the excipient may include a sweetener. By way of non-limiting example, the sweetener may be selected from glucose (corn syrup), dextrose, invert sugar, fructose, and mixtures thereof (when not used as a carrier); saccharin and its various salts such as the sodium salt; dipeptide sweeteners such as aspartame; dihydrochalcone compounds, glycyrrhizin; *stevia*-derived sweeteners; chloro derivatives of sucrose such as sucralose; sugar alcohols such as sorbitol, mannitol, xylitol, and the like. Also contemplated are hydrogenated starch hydrolysates and the synthetic sweetener 3,6-dihydro-6-methyl-1,2,3-oxathiazin-4-one-2,2-dioxide, particularly the potassium salt (acesulfame-K), and sodium and calcium salts thereof. In particular embodiments, the pharmaceutical composition may be formulated for oral administration and include one or more of the following flavorant (e.g., sweetening agents): sucralose, MagnaSweet®, Di-Pac® compressible sugar (i.e., a 97:3 mixture of sucrose and maltodextrin), Thaumatin T200X, Talin-Pure, OptisweetSD, *stevia* extract rebaudioside A, and/or neotame.

In some embodiments, the pharmaceutical composition that may be formulated for oral administration can include one or more of the following flavoring agents and/or flavor-masking agents (e.g., sweetening agents): sucralose; a dispersion of licorice, licorice derivatives, and licorice extract (glycyrrhizic acid/monoammonium glycyrrhizinate); MagnaSweet®; a blend of sodium saccharin and neohesperidin dihydrochalcone (Optisweet™ SD), 97:3 (w/w) mixture of sucrose and maltodextrin (Di-Pac®), thaumatin 7% (sweetener) blended with an inactive maltodextrin (Thaumatin T200X), pure thaumatin (Talin-Pure), *stevia* extract rebaudioside A (steviol glycosides), neotame, and/or polyols (sugar alcohols), such as sorbitol, maltitol, isomalt, xylitol, and glycerin.

As used herein "MagnaSweet®" refers to a composition consisting essentially of one or more sweeteners selected from the group consisting of glycyrrhizic acid (GA), monoammonium glycyrrhizinate (MAG), rebaudioside A, and glycerin. In some embodiments, the MagnaSweet® consists essentially of glycyrrhizic acid (GA), monoammonium glycyrrhizinate (MAG), rebaudioside A, and glycerin. In other embodiments, the MagnaSweet® consists essentially of glycyrrhizic acid (GA), monoammonium glycyrrhizinate (MAG), and glycerin. In some embodiments, the MagnaSweet® comprises from about 0.5% to about 25% GA/MAG, from about 0% to about 15% rebaudioside A, and from about 75% to about 99.5% glycerin. In other embodiments, the MagnaSweet® comprises from about 1.5% to about 17% GA/MAG, from about 0% to about 7.5% rebaudioside A, and from about 83% to about 91% glycerin. In exemplary embodiments, the MagnaSweet® comprises about 1.5% GA/MAG, about 7.5% rebaudioside A, and about 91% glycerin. In other exemplary embodiments, the MagnaSweet® comprises about 9% GA/MAG and about 91% glycerin. In another exemplary embodiment, the MagnaSweet® comprises about 17% GA/MAG and about 83% glycerin.

In particular, some sugar-containing sweeteners, such as saccharose-containing materials, sucrose, glucose, fructose, and maltodextrin, may at least partially degrade the capromorelin within the composition. Accordingly, large concentrations of some sugar-containing sweeteners should be avoided.

In exemplary embodiments, the flavoring agents or masking agents can comprise at least one of thaumatin, sucralose, neotame, sodium saccharain, neohesperidin dihydrochalcone, rebaudioside A, steviol glycosilde, licorice, glycyrrhizic acid, monoammonium glycyrrihizinate, sucrose, glucose, fructose, maltodextrin, sorbitol, maltitol, isomalt, glycerol, and a vanilla-comprising composition.

The excipient may include a taste-masking agent. Taste-masking materials include cellulose hydroxypropyl ethers (HPC); low-substituted cellulose hydroxypropyl ethers (L-HPC); cellulose hydroxypropyl methyl ethers (HPMC); methylcellulose polymers and mixtures thereof polyvinyl alcohol (PVA); hydroxyethylcelluloses; carboxymethylcelluloses and salts thereof; polyvinyl alcohol and polyethylene glycol co-polymers; monoglycerides or triglycerides; polyethylene glycols; acrylic polymers; mixtures of acrylic polymers with cellulose ethers; cellulose acetate phthalate; and combinations thereof.

In some embodiments, the flavorant may comprise a percent weight per final volume of the pharmaceutical composition form about 50% to about 0.001%, depending on the agent selected, such as from about 40% to about 0.01%, from about 30% to about 0.01%, from about 1% to about 30%, or from about 5% to about 15%. As previously mentioned, the pharmaceutical composition may include more than one flavorant.

(ii) Dosage Form

The pharmaceutical compositions detailed herein may be manufactured in one or several dosage forms. Suitable dosage forms include tablets, including suspension tablets, chewable tablets, effervescent tablets or caplets; pills; powders such as a sterile packaged powder, a dispensable powder, and an effervescent powder; capsules including both soft or hard gelatin capsules such as HPMC capsules; lozenges; a sachet; a sprinkle; a reconstitutable powder or shake; a troche; pellets such as sublingual or buccal pellets; granules; liquids for oral or parenteral administration; suspensions; emulsions; semisolids; or gels. Other suitable dosage forms include transdermal systems or patches. The transdermal system may be a matrix system, a reservoir system, or a system without rate-controlling membranes.

The dosage forms may be manufactured using conventional pharmacological techniques. Conventional pharmacological techniques include, for example, one or a combination of methods: (1) dry mixing, (2) direct compression, (3) milling, (4) dry or non-aqueous granulation, (5) wet granulation, or (6) fusion. See, e.g., Lachman et al., *The Theory and Practice of Industrial Pharmacy* (1986). Other methods include, e.g., prilling, spray drying, pan coating, melt granulation, granulation, wurster coating, tangential coating, top spraying, extruding, coacervation and the like.

The amount of active ingredient that is administered to a subject can and will vary depending upon a variety of factors such as the age and overall health of the subject, and the particular mode of administration. Those skilled in the art will appreciate that dosages may also be determined with guidance from *Goodman & Gilman's The Pharmacological Basis of Therapeutics*, Tenth Edition (2001), Appendix II, pp. 475-493, and the Physicians' Desk Reference (PDR).

(II) Methods for Treatment Using a Grapiprant Composition

Another aspect of the present disclosure encompasses a method for treating pain or inflammation in a non-human animal in need thereof. The method comprises administering to the non-human animal a pharmaceutical composition comprising a therapeutically effective amount of grapiprant.

Dosage of grapiprant may range from about 0.01 milligrams of grapiprant per kilogram of bodyweight of the non-human animal ("mg/kg") to about 75 mg/kg, such as about 0.1 mg/kg to about 7.5 mg/kg. In some embodiments, the grapiprant dosage may range from about 0.75 mg/kg to about 6 mg/kg. In some embodiments, the grapiprant dosage may range from about 6 mg/kg to about 50 mg/kg. In other embodiments, the grapiprant dosage may be at least about 0.1 mg/kg, about 0.2 mg/kg, about 0.3 mg/kg, about 0.33 mg/kg, about 0.5 mg/kg, about 0.75 mg/kg, about 1.0 mg/kg, about 2.0 mg/kg, about 3.0 mg/kg, about 4.0 mg/kg, about 5.0 mg/kg, about 6.0 mg/kg, about 9.0 mg/kg, or about 15 mg/kg.

In exemplary embodiments, a non-human animal may receive about a 2 mg/kg dosage of grapiprant. In another exemplary embodiment, a non-human animal may receive about a 3 mg/kg dosage of grapiprant. In one exemplary embodiment, a non-human animal may receive about a 4 mg/kg dosage of grapiprant. In another exemplary embodiment, a non-human animal may receive greater than about a 2 mg/kg dosage of grapiprant. In yet another exemplary embodiment, a non-human animal may receive less than about a 50 mg/kg dosage of grapiprant. In one exemplary embodiment, a non-human animal may receive less than about a 6 mg/kg dosage of grapiprant.

In one embodiment, a non-human animal may receive about a 3 mg/kg dosage of grapiprant. In one embodiment, a non-human animal may receive about a 6 mg/kg dosage of grapiprant. In one embodiment, a non-human animal may receive about a 9 mg/kg dosage of grapiprant. In one embodiment, a non-human animal may receive about a 15 mg/kg dosage of grapiprant. In one embodiment, a non-human animal may receive about a 50 mg/kg dosage of grapiprant.

The dosing may be divided into multiple treatment regimens, depending on severity of the indications of the non-human animal. For example, in some embodiments, the pharmaceutical composition may be administered to the non-human animal in need thereof at least once daily, such as at least twice daily, at least thrice daily, or at multiple times each day. In other embodiments, the pharmaceutical composition may be administered to the non-human animal in need thereof about 10 hours to about 18 hours before surgery, such as about 11 hours, about 12 hours, about 13 hours, about 14 hours, about 15 hours, about 16 hours, about 17 hours, or about 18 hours before surgery.

The dosage of grapiprant may also be expressed in terms of a dosage rate; that is, the total amount of grapiprant provided to a non-human animal per kilogram bodyweight over the course of a 24-hour period (mg/kg/day). In some embodiments, the grapiprant dosage rate may range from about 1.5 mg/kg/day to about 12 mg/kg/day. In other embodiments, the grapiprant dosage may be at least about 0.2 mg/kg/day, about 0.4 mg/kg/day, about 0.6 mg/kg/day, about 0.66 mg/kg/day, about 1.0 mg/kg/day, about 1.5 mg/kg/day, about 2.0 mg/kg/day, about 4.0 mg/kg/day, about 6.0 mg/kg/day, about 8.0 mg/kg/day, about 10.0 mg/kg/day, about 12.0 mg/kg/day, or about 15.0 mg/kg/day. In exemplary embodiments, the non-human animal may receive grapiprant at a dosage rate of about 1 to about 8 mg/kg/day. In other exemplary embodiments, the non-human animal may receive grapiprant at a dosage rate of about 2 to about 4 mg/kg/day. In one embodiment, the non-human animal may receive grapiprant at a dosage rate of about 3 to about 15 mg/kg/day.

Dosing may be in the form of solid or liquid formulations. For example, some non-human animals, such as dogs, may receive one or more solid oral formulations, such as a pharmaceutical composition formulated for administration via capsules, gel caps, gel-like liquids (i.e., viscous liquids), solutions, suspensions, pills, caplets, tablets, or other solid, liquid, or nebulized forms. For example, the capsules or other forms may include different concentrations of grapiprant to enable dosing of non-human animals of a plurality of bodyweights. By way of example only, capsules may be manufactured with a grapiprant concentration of 20 mg per capsule, 35 mg per capsule, or 75 mg per capsule. As a result, different combinations of capsules may be administered to the non-human animals in need of treatment. By way of example only, a non-human animal weighing about 15 kg and placed on a 3-mg/kg treatment regimen would use about 45 mg of grapiprant per dose. Accordingly, the non-human animal may receive two 20-mg capsules to provide a dose of grapiprant that is close to 45 mg (i.e., within 5 and 10 milligrams of the desired dose based on bodyweight or within a dosing band). Non-human animals of other sizes placed on other treatment regimens may be similarly treated to provide an efficacious amount of grapiprant.

The administering may achieve a $C_{max}$ of grapiprant of about 375 ng/mL to about 10000 ng/mL at a $T_{max}$ of about 0.4 to about 3.4 hours, such as a $C_{max}$ of grapiprant of 750 about ng/mL to about 8000 ng/mL, or of about 1300 ng/mL to about 4000 ng/mL. In other embodiments, the $C_{max}$ of grapiprant may also be achieved at a $T_{max}$ of about 0.7 to about 1.7 hours, such as a $T_{max}$ of about 0.5 to about 1.0 hours.

In some embodiments, the $C_{max}$ may vary in different non-human animals, therefore the $C_{max}$ could be even higher. For example, the $C_{max}$ may be about 375 ng/mL, about 400 ng/mL, about 500 ng/mL, about 600 ng/mL, about 700 ng/mL, about 800 ng/mL, about 900 ng/mL, about 1000 ng/mL, about 1500 ng/mL, about 2000 ng/mL, about 2500 ng/mL, about 3000 ng/mL, about 3500 ng/mL, about 4000 ng/mL, about 4500 ng/mL, about 5000 ng/mL, about 5500 ng/mL, about 6000 ng/mL, about 6500 ng/mL, about 7000 ng/mL, about 7500 ng/mL, about 8000 ng/mL, about 8500 ng/mL, about 9000 ng/mL, about 9500 ng/mL, or about 10000 ng/mL. In exemplary embodiments, the $C_{max}$ of grapiprant may be 375 ng/mL to 10000 ng/mL. In other exemplary embodiments, the $C_{max}$ of grapiprant may be 750 ng/mL to 8000 ng/mL. In yet other exemplary embodiments, the $C_{max}$ of grapiprant may be 1300 ng/mL to 4000 ng/mL. In some embodiments, the $C_{max}$ of grapiprant may be greater than 375 ng/mL. In other embodiments, the $C_{max}$ of grapiprant may be less than 10000 ng/mL.

In other embodiments, the $T_{max}$ may occur in an individual non-human animal at a 30-minute, 1-hour, or 2-hour time interval, with the range being from about 30 minutes to 2 hours to reach $T_{max}$. The $T_{max}$ may be about 0.4 hours, about 0.5 hours, about 0.6 hours, about 0.7 hours, about 0.8 hours, about 0.9 hours, about 1.0 hours, about 1.1 hours, about 1.2 hours, about 1.3 hours, about 1.4 hours, about 1.5 hours, about 1.6 hours, about 1.7 hours, about 1.8 hours, about 1.9 hours, about 2.0 hours, about 2.2 hours, about 2.4 hours, about 2.6 hours, about 2.8 hours, about 3.0 hours, about 3.2 hours, or about 3.4 hours. In one embodiment, the $T_{max}$ may be from 0.4 to 3.4 hours. In exemplary embodiments, the $T_{max}$ may be from 0.7 to 1.7 hours. In other exemplary embodiments, the $T_{max}$ may be from 0.5 to 1.0 hours. In some embodiments, the $T_{max}$ may be greater than 0.4 hours. In other embodiments, the $T_{max}$ may be less than 3.4 hours.

The AUC may range from about 1000 hr*ng/mL to about 11000 hr*ng/mL. In exemplary embodiments, the AUC may range from about 1000 hr*ng/mL to about 1500 hr*ng/mL, from about 1500 hr*ng/mL to about 2000 hr*ng/mL, from about 2000 hr*ng/mL to about 2500 hr*ng/mL, from about 2500 hr*ng/mL to about 3000 hr*ng/mL, from about 3000 hr*ng/mL to about 3500 hr*ng/mL, from about 3500 hr*ng/mL to about 4000 hr*ng/mL, from about 4000 hr*ng/mL to about 4500 hr*ng/mL, from about 4500 hr*ng/mL to about 5000 hr*ng/mL, from about 5000 hr*ng/mL to about 5500 hr*ng/mL, from about 5500 hr*ng/mL to about 6000 hr*ng/mL, from about 6000 hr*ng/mL to about 6500 hr*ng/mL, from about 6500 hr*ng/mL to about 7000 hr*ng/mL, from about 7000 hr*ng/mL to about 7500 hr*ng/mL, from about 7500 hr*ng/mL to about 8000 hr*ng/mL, from about 8000 hr*ng/mL to about 8500 hr*ng/mL, from about 8500 hr*ng/mL to about 9000 hr*ng/mL, from about 9000 hr*ng/mL to about 9500 hr*ng/mL, from about 9500 hr*ng/mL to about 10000 hr*ng/mL, from about 10000 hr*ng/mL to about 10500 hr*ng/mL, or from about 10500 hr*ng/mL to about 11000 hr*ng/mL.

The half-life ($t_{1/2}$) may range from about 1.5 hours to about 9 hours. In some embodiments, the $t_{1/2}$ may range from about 3 hours to about 14 hours. In exemplary embodiments, the $t_{1/2}$ may range from about 1.5 hours to about 2 hours, from about 2 hours to about 2.5 hours, from about 2.5 hours to about 3 hours, from about 3 hours to about 3.5 hours, from about 3.5 hours to about 4 hours, from about 4 hours to about 4.5 hours, from about 4.5 hours to about 5 hours, from about 5 hours to about 5.5 hours, from about 5.5 hours to about 6 hours, from about 6 hours to about 6.5 hours, from about 6.5 hours to about 7 hours, from about 7 hours to about 7.5 hours, from about 7.5 hours to about 8 hours, from about 8 hours to about 8.5 hours, from about 8.5 hours to about 9 hours, from about 9 hours to about 9.5 hours, from about 9.5 hours to about 10 hours, from about 10 hours to about 10.5 hours, from about 10.5 hours to about 11 hours, from about 11 hours to about 11.5 hours, from about 11.5 hours to about 12 hours, from about 12 hours to about 12.5 hours, from about 12.5 hours to about 13 hours, from about 13 hours to about 13.5 hours, or from about 13.5 hours to about 14 hours.

The duration of administration can and will vary. In general, the pharmaceutical composition may be administered to a non-human animal in need thereof for about 6 days to about 9 months. In particular embodiments, the pharmaceutical composition may be administered to a non-human animal in need thereof for about 6 days, for about 7 days, for about 8 days, for about 9 days, for about 10 days, for about 11 days, for about 12 days, for about 13 days, for about 14 days, for about 15 days, for about 16 days, for about 17 days, for about 18 days, for about 19 days, for about 20 days, for about 21 days, for about 22 days, for about 23 days, for about 24 days, for about 25 days, for about 26 days, for about 27 days, or for about 28 days.

In exemplary embodiments, the pharmaceutical composition may be administered to a non-human animal in need thereof for about 9 days to about 21 days. In other exemplary embodiments, the pharmaceutical composition may be administered to a non-human animal in need thereof for about 12 days to about 14 days. In some embodiments, the pharmaceutical composition may be administered to a non-human animal in need thereof for about 1 month, about 2 months, about 3 months, about 4 months, about 5 months, about 6 months, about 7 months, about 8 months, or about 9 months. In one embodiment, the pharmaceutical composition may be administered to a non-human animal in need thereof for about 28 days.

In some exemplary embodiments, the pharmaceutical formulation may administered twice daily at a dosage of about 2 mg/kg/day to about 4 mg/kg/day for about 9 days to about 21 days, and the administering may achieve a $C_{max}$ of grapiprant of about 750 ng/mL to about 2200 ng/mL at a $T_{max}$ of about 0.7 to about 1.7 hours.

In some embodiments, the pharmaceutical composition may comprise a liquid oral formulation that may be used in a manner similar to the above solid oral formulation. Additionally, the liquid formulations may be administered in a syringe or sprayed on to the animal's food, treats, or chews. Where the non-human animal is livestock, the pharmaceutical composition may be sprayed onto or incorporated into the feed. For example, the liquid formulation may be prepared to comprise about 20 mg/mL, about 30 mg/mL, about 40 mg/mL, or about 60 mg/mL of grapiprant within the liquid formulation.

Similar to the solid formulations discussed above, the different concentrations of the liquid formulation may be used to dosing non-human animals of a plurality of bodyweights. As a result, different volumes of the different solutions may be administered to the non-human animals to provide a dose of grapiprant. By way of example only, a non-human animal weighing about 15 kg and placed on a 3 mg/kg treatment regimen would use about 45 mg of grapiprant per dose. Accordingly, the non-human animal may receive about 2.3 mL of the 20 mg/mL solution or 1.1 mL of the 40 mg/mL solution to provide a dose of grapiprant close to 45 mg. Similarly, if the same non-human animal was placed on a 4.5 mg/kg treatment regimen, the animal could receive 2.3 mL of the 30 mg/mL solution or 1.1 mL of the 60 mg/mL solution to provide a dose of grapiprant close to 67.5 mg (i.e., the dose a 15 kg animal should receive on this treatment regimen). Other non-human animals of other sizes placed on other treatment regimens may be similarly treated to provide an efficacious amount of grapiprant.

In some embodiments, the pharmaceutical composition may be administered using any one of a plurality of routes of administration. The pharmaceutical composition may be orally, parenterally, and/or topically administered. For example, the pharmaceutical composition may be orally formulated in a liquid and/or a solid formulation so that the composition may be administered using at least one of a spray, a syringe, a pill, a tablet, a caplet, a gel-cap, or an otherwise liquid-based administration scheme.

In other embodiments, the pharmaceutical composition may be formulated for administration via subcutaneous, intradermal, intravenous, intramuscular, intracranial, intraperitoneal, or intrathecal administration (e.g., via an injection or composition-dispensing pump). The pharmaceutical composition may be formulated as a parenterally administered depot formulation that can be configured for extended release of the grapiprant (e.g., release over the period of multiple days to multiple months). Moreover, the pharmaceutical composition may be administered as a gel that contacts the skin or other tissue of the animals and is accordingly absorbed therethrough. Alternatively, the pharmaceutical composition may be administered using an electrophoretic system to drive the composition into circulation of the non-human animal. In yet other embodiments, the pharmaceutical composition may be formulated for transdermal and/or transmucosal administration (e.g., via a buccal film or patch that is applied to the inner cheek of the non-human animal). In addition, in some embodiments, the pharmaceutical composition may be administered intranasally or in the form of one or more suppositories. In some embodiments, the pharmaceutical composition may be formulated as an implant that may be disposed within the soft tissue of the non-human animals. For example, the composition-containing implant may be implanted into the cutaneous, subcutaneous, and/or muscle tissue of the non-human animal for extended release. Moreover, the pharmaceutical composition may also be formulated to be administered to the skin of the non-human animal in a "spot-on" manner. In yet other embodiments, the pharmaceutical composition may be formulated for any other suitable route of administration known in the art. In exemplary embodiments, the pharmaceutical formulation may be administered orally and may be selected from any pharmaceutical formulation described above in Section (I).

In some embodiments, the pharmaceutical composition may be administered to the non-human animal as a part of a daily feeding regimen. For example, the pharmaceutical composition may be formulated to be mixed with the feed or other food product intended for the non-human animal such that, as the non-human animal intakes its daily food (e.g., kibble or soft food), the non-human animal also consumes the pharmaceutical composition. In particular, the pharmaceutical composition may be formulated as a liquid or a powder so that before feeding the non-human animal, the pharmaceutical composition may be applied (e.g., sprayed) onto the food. Moreover, in some embodiments, the food provided to the non-human animals may be provided with the pharmaceutical composition already added such that the non-human animal's caretaker need only provide the medicated food to the non-human animal.

Other food products provided to the non-human animal may be supplemented with the grapiprant composition. For example, soft or hard treats or chews (e.g., rawhide or other animal-based products given to non-human animals for enjoyment and/or enrichment) may be supplemented with the grapiprant composition, where the grapiprant composition may either be incorporated into the treat or chew or sprayed onto the treat or chew. In some aspects, the treats or chews may be purchased in a form that already includes the grapiprant composition. In other aspects, the grapiprant composition may be later added to the treats or chews by the individual feeding the animal.

Moreover, in some embodiments, the kibble, treats, and/or chews may be mixed with a maintenance level dosage of the grapiprant-containing composition. Preferably, an animal receiving the maintenance level dosage is able to maintain a certain level of food consumption. For example, as discussed above, a maintenance dose (e.g., 0.2 mg/kg) can be provided to the animals on a regular or irregular basis to provide lower doses of the active ingredient. By providing these maintenance doses with the food products (e.g., kibble), treats, and/or chews, the animals can relatively enjoy the experience of receiving the maintenance doses such that little to no active ingredient is lost in the administration process.

Definitions

The compounds described herein have asymmetric centers. Compounds of the present disclosure containing an asymmetrically substituted atom may be isolated in optically active or racemic form. All chiral, diastereomeric, racemic forms and all geometric isomeric forms of a structure are intended, unless the specific stereochemistry or isomeric form is specifically indicated.

The term "animal" designates non-human animals, such as "livestock" and "companion animals." "Livestock" includes cows, sheep, pigs, poultry (e.g., chickens, turkeys, quail, etc.) goats, llamas, and other similar animals. The term "companion animal" includes, but is not limited, to dogs, cats, rabbits, ferrets, horses, and hamsters. In exemplary embodiments, the companion animal is a dog, cat, or horse.

The term "composition" applies to any solid object, semisolid, or liquid composition designed to contain a specific pre-determined amount (dose) of a certain ingredient, for example, an active pharmaceutical ingredient, as previously mentioned and as discussed below. Suitable compositions may be pharmaceutical drug delivery systems, including those for oral administration, buccal administration, rectal administration, topical or mucosal administration, or subcutaneous implants, or other implanted drug delivery systems; or compositions for delivery minerals, vitamins and other nutraceuticals, oral care agents, flavorants, flavor-masking agents, and the like. In one embodiment, the compositions are generally liquid, however they may contain solid or semi-solid components. Generally, the dosage form is an orally administered system for delivering a pharmaceutical active ingredient to the alimentary canal of a companion animal.

The phrase "therapeutically effective amount" refers to an amount effective, at dosages and for periods of time necessary, to achieve the desired therapeutic result. A therapeutically effective amount of grapiprant may be determined by a person skilled in the art (e.g., a veterinarian) and may vary according to factors such as the clinical state, age, sex, and weight of the companion animal, bioavailability of grapiprant, and the ability of the active agent(s) to elicit a desired response in the companion animal. A therapeutically effective amount is also one in which any toxic or detrimental effects of the active agent(s), are outweighed by the therapeutically beneficial effects. A therapeutically effective amount also encompasses an amount that is effective, at dosages and for periods of time necessary, to achieve the desired result (e.g., weight gain through the addition of lean muscle mass).

The term "q.s." means to add a quantity (e.g., volume or mass) of an ingredient until the final amount (e.g., volume or mass) is reached.

The term "w/v" designates a concentration of a substance as measured in weight of the substance per volume of a solution or composition.

When introducing elements of the present disclosure or the embodiments(s) thereof, the articles "a," "an," "the," and "said" are intended to mean that there are one or more of the elements. The terms "comprising," "including," and "having" are intended to be inclusive and mean that there may be additional elements other than the listed elements.

Having described the disclosure in detail, it will be apparent that modifications and variations are possible without departing from the scope of the disclosure defined in the appended claims.

EXAMPLES

The following examples are included to demonstrate certain embodiments of the disclosure. It should be appreciated by those of skill in the art that the techniques disclosed in the examples represent techniques discovered by the inventors to function well in the practice of the disclosure. Those of skill in the art should, however, in light of the present disclosure, appreciate that many changes can be made in the specific embodiments that are disclosed and still obtain a like or similar result without departing from the spirit and scope of the disclosure, therefore all matter set forth is to be interpreted as illustrative and not in a limiting sense.

Example 1—Palatability Study of Grapiprant in Dogs

Fifty privately-owned pet dogs were used in the study. The dogs were a mixture of breeds, sexes (male and female, all neutered), aged from 1.5 years to 13 years, and weighing from 14.5 to 113 pounds. The treatment was a flavored tablet containing 12.5 mg of grapiprant. Four different flavored tablets (A, B, C, and D) were used for each dog, regardless of bodyweight. The flavors used were beef, pork liver, and two other flavor combinations. All test articles were manufactured by Argenta Manufacturing, Manurewa, Auckland, New Zealand. Composition of the test articles are shown at Table 1.

TABLE 1

Grapiprant formulations used in the palatability study.

| Material Name | Tablet A | Tablet B | Tablet C | Tablet D |
|---|---|---|---|---|
| | Formula (% w/w) | | | |
| Grapiprant | 2.4 | 2.4 | 2.4 | 2.4 |
| Microcrystalline Cellulose | 40.0 | 35.0 | 35.0 | 35.0 |
| Lactose Supertab Spray Dried | 45.6 | 40.6 | 40.6 | 40.6 |
| Sodium Starch Glycolate | 5.0 | 5.0 | 5.0 | 5.0 |
| Flavorant | Protex 3496 "A" Flavor Powder 5.0 | Flavor Powder-Spray-Dried Pork Liver 15.0 | Flavor Powder-Artificial Beef PC-0125 15.0 | Flavor Powder-Artificial PC-0335 15.0 |
| Colloidal Silicon Dioxide | 0.5 | 0.5 | 0.5 | 0.5 |
| Magnesium Stearate | 1.5 | 1.5 | 1.5 | 1.5 |

TABLE 2

Palatability Evaluation, Results.

| Response | Tablet A N = 12 | Tablet B N = 13 | Tablet C N = 12 | Tablet D N = 13 |
|---|---|---|---|---|
| Dog ate completely, immediately | 1 (8.3%) | 11 (84.6%) | 8 (66.7%) | 7 (53.8%) |
| Dog played with, but eventually consumed | 2 (16.7%) | 1 (7.7%) | 2 (16.7%) | 3 (23.1%) |
| Dog put in mouth, but spit out | 3 (25.0%) | 0 (0.0%) | 1 (8.3%) | 1 (7.7%) |
| Dog completely refused | 6 (50.0%) | 1 (7.7%) | 1 (8.3%) | 2 (15.4%) |
| Acceptability/Palatability | 3 (25.0%) | 12 (92.3%) | 10 (83.3%) | 10 (76.9%) |
| Palatable to dog, as assessed by owner | 3 (25.0%) | 11 (84.6%) | 10 (83.3%) | 9 (69.2%) |
| Unpalatable to dog, as assessed by owner | 9 (75.0%) | 2 (15.4%) | 2 (16.7%) | 4 (30.8%) |

This study was a randomized, blinded, non-GCP clinical trial. Based on these data, tablet B was preferred by the test animals, followed by tablets C and D. Tablet A was rejected by most (75.0%) of dogs tested. In treatment groups A and C, the owner's assessment of palatability coincided with whether the dogs consumed the tablet. In these two cases, the dogs did eventually consume the tablet; however, the owners reported that their dogs probably did not find the tablets palatable. Overall, Tablet B was found to be the most palatable by both metrics. No statistical tests were applied to these data.

Example 2—Another Palatability Study of Grapiprant in Dogs

A total of 40 privately-owned dogs were presented at two veterinary clinics. The dogs were a mixture of breeds, sexes (male and female, all neutered except two females), aged from 15 months to 13 years, 10 months, and weighing from 19.6 to 109 pounds. In total, four protocol deviations related to selection criteria.

The treatment was a flavored tablet containing 20 mg of grapiprant. Four different flavored tablets (A27, A29, A31, and A34) were used for all dogs regardless of weight. The flavoring agent used was derived from pork liver. The tablets differed in the amount (5%, 10% or 15%) of flavoring agent included. Two of the formulations (labeled A27 and A34) evaluated contained 15% pork liver flavoring; the difference between the two formulations lies in the surfactant component: Formulation A27 contained poloxamer, while Formulation A34 contained sodium laurel sulfate. All test articles were manufactured by Argenta Manufacturing (Manurewa, Auckland, New Zealand) and received by Ricerca Laboratories (Concord, OH). Composition of the test articles was as shown in Table 3.

TABLE 3

Formulations of grapiprant.

| Material* | Formulation A27 | Formulation A29 | Formulation A31 | Formulation A34 |
|---|---|---|---|---|
| Grapiprant | 8.0 | 8.0 | 8.0 | 8.0 |
| Lactose (Super-Tab) | 36.0 | 36.0 | 41.0 | 35.0 |
| Sodium Starch Glycolate | 5.0 | 5.0 | 5.0 | 5.0 |
| Microcrystalline Cellulose | 28.0 | 38.0 | 28.0 | 28.0 |
| Colloidal Silicon Dioxide | 0.5 | 0.5 | 0.5 | 0.5 |
| Magnesium Stearate | 1.5 | 1.5 | 1.5 | 1.5 |
| Flavor Powder-Pork Liver | 15.0 | 5.0 | 10.0 | 15.0 |
| Copovidone (Kollidon VA64) | 5.0 | 5.0 | 5.0 | 5.0 |
| Surfactant | 1.0 | 1.0 | 1.0 | 2.0 |

*Amounts of each component are listed as weight percent of the total formulation.

After eating the tablet (if applicable), the owner's assessment of whether or not he or she believed that the dog found the tablet palatable was recorded. Dogs were observed for 5 minutes for regurgitation/vomiting, or adverse reactions to the administration (e.g., frothing/foaming, pawing at the mouth, other abnormal behaviors). Dogs' acceptance or rejection of the study product was recorded.

The relationship between each adverse event and the test article was classified in relationship to the treatment as follows:
  1=Unrelated: Clearly pre-existing or caused by a specific extraneous event.
  2=Possibly related: Possible drug association as suggested by the relationship of adverse event with treatment and external events.
  3=Related: Strong suspicion of drug association when type, time course, and relationship of adverse event to treatment and external events are considered.

Data Analysis and Results. Upon entry into the database, categorical summary statistics were performed to evaluate the palatability of the four formulations. The results are summarized in Table 4 below. "Acceptability/Palatability" is defined as the percentage of dogs offered each formulation who consumed the tablet within the 5-minute period, whether they consumed it readily or played with the tablet before consuming it.

TABLE 4

Palatability Evaluation Results

| Dogs' Behavior | Formulation A27 N = 9 | Formulation A29 N = 11 | Formulation A31 N = 10 | Formulation A34 N = 10 |
|---|---|---|---|---|
| Dog ate completely and Immediately | 4 | 3 | 4 | 2 |
| Dog played with, but eventually consumed | 1 | 2 | 1 | 3 |
| Dog put in mouth, but spit out | 1 | 1 | 1 | 1 |
| Dog completely refused | 3 | 5 | 4 | 4 |
| Acceptability/Palatability | 55.6% | 45.5% | 50.0% | 50.0% |
| Palatable to Dog, as assessed by Owner | 55.6% | 36.4% | 40.0% | 50.0% |
| Unpalatable to Dog, as assessed by Owner | 44.4% | 63.6% | 60.0% | 50.0% |

Based on these data, Formulation A27 was most acceptable to the test animals, with 55.6% consuming the tablet without encouragement. Formulations A31 and A34 were accepted and rejected by an equal number (50%) of dogs tested. Formulation A29 was rejected by more than half (55.4%) of dogs tested. Although the palatability estimates did not differ appreciably among the four formulations, there may be a trend toward a dose-response effect in the level of flavoring compound: 5% pork liver powder <[10% pork liver=15% pork liver (sodium laurel sulfate as surfactant)] <15% pork liver (poloxamer). In all but two cases (Formulation A31 and Formulation A29) the owner's assessment of palatability coincided with whether or not the dogs consumed the tablet.

In these cases, the dog did eventually consume the tablet; however, the owners reported that the dogs probably did not find the tablet palatable. No statistical tests were applied to the data. In this single-dose study, no adverse events were reported, nor were there any observations of unusual behaviors (frothing/foaming, pawing at the mouth, other abnormal behaviors).

Example 3—Pharmacokinetic Studies of Grapiprant in Dogs

The objective of this study was to compare the pharmacokinetic profile of several tablet formulations of grapiprant to capsule and aqueous methylcellulose suspension formulations of grapiprant with 20-mg doses. Appropriate amounts of the test article/excipient mixture were placed into gelatin capsules to provide each animal with 20 mg of grapiprant. As the grapiprant content in the excipient blend was 45% of the mixture weight, the total weight of the blend in each capsule was 0.0440 g. The weight tolerance was within ±0.005 g of the nominal capsule content weight.

For the aqueous suspensions (Group 2), the vehicle was 0.5% methyl cellulose (400 centipoise) in water. A 0.3-mg/mL suspension of grapiprant was prepared by adding grapiprant to a calibrated beaker and adding about 60-90% of the 0.5% aqueous methylcellulose to the beaker. A homogenizer was used to blend the material. A stir bar was added to the beaker, and the suspension was stirred for about 5 minutes. The stir bar was removed temporarily to adjust the volume with additional vehicle, and then the suspension was stirred for another 5 minutes before being transferred to a labeled dosing container. The formulation was continuously stirred at the time of dose administration.

A single oral dose by capsule, suspension, or tablet was given to dogs shown in Table 5.

TABLE 5

Formulations used in this study.

| Group | Number of Animals | Formulation | Nominal Dose Level (mg/kg)* |
|---|---|---|---|
| 1 | 5 | 20 mg API in capsule | 2 |
| 2 | 5 | 0.3 mg/mL methylcellulose suspension Dose volume: 6.67 mL/kg | 2 |
| 3 | 5 | 20 mg tablet, Formulation A29 | 2 |
| 4 | 5 | 20 mg tablet, Formulation A34 | 2 |
| 5 | 5 | 20 mg tablet, Formulation A31 | 2 |
| 6 | 5 | 20 mg tablet, Formulation 120314-1 | 2 |

*based on a 10-kg animal. Only whole tablets were used in Groups 3-6.

Statistical analyses were conducted to determine differences in $C_{max}$, $T_{max}$, and AUCmax Values were normalized by mg/kg, and group means and standard deviations were calculated for numeric data. The actual administered doses ranged from 1.81 to 2.82 mg/kg, and averaged 2.2 mg/kg. No animal was found dead or deemed moribund during the study. All animals were normal at the scheduled observation time of 2 hours postdose. The mean pharmacokinetic parameters, in addition to the dose-normalized $C_{max}$ and $AUC_{0-\infty}$, are shown in Table 6.

TABLE 6

Mean Grapiprant Pharmacokinetic Parameters in Male Dogs on Day 0.

| Group | Dose (mg/kg) | $C_{max}$ (ng/mL) | $T_{max}$ (hr) | $AUC_{last}$ (hr*ng/mL) | $AUC_{0-\infty}$ (hr*ng/mL) | $t_{1/2}$ (hr) | $C_{max}$/Dose (ng/mL)/(mg/kg) | $AUC_{0-\infty}$/Dose (hr*ng/mL)/(mg/kg) |
|---|---|---|---|---|---|---|---|---|
| 1 | 2.16 | 804 | 1.08 | 1580 | 1640 | 5.5 | 359 | 724 |
| 2 | 2.00 | 751 | 0.786 | 1650 | 1870 | 4.1 | 376 | 937 |
| 3 | 2.2 | 1200 | 0.891 | 2330 | 2340 | 2.17 | 546 | 1070 |

TABLE 6-continued

Mean Grapiprant Pharmacokinetic Parameters in Male Dogs on Day 0.

| Group | Dose (mg/kg) | $C_{max}$ (ng/mL) | $T_{max}$ (hr) | $AUC_{last}$ (hr*ng/mL) | $AUC_{0-\infty}$ (hr*ng/mL) | $t_{1/2}$ (hr) | $C_{max}$/Dose (ng/mL)/(mg/kg) | $AUC_{0-\infty}$/Dose (hr*ng/mL)/(mg/kg) |
|---|---|---|---|---|---|---|---|---|
| 4 | 2.2 | 887 | 0.995 | 2050 | 2320 | 8.58 | 409 | 1160 |
| 5 | 2.29 | 697 | 1.4 | 1690 | 1860 | 5.87 | 311 | 757 |
| 6 | 2.14 | 816 | 1.09 | 2020 | 2560 | 7.52 | 377 | 1150 |

Following a single oral dose of 20 mg grapiprant capsule to Group 1 dogs, the mean $T_{max}$ was 1.08 hours, the mean terminal half-life was 5.5 hours, the mean $C_{max}$ was 804 ng/mL, and the mean $AUC_{0-\infty}$ was 1640 hr*ng/mL. Following a single oral dose of 2 mg/kg grapiprant suspension to Group 2 dogs, the mean $T_{max}$ was 0.786 hours, the mean terminal half-life was 4.1 hours, the mean $C_{max}$ was 751 ng/mL, and the mean $AUC_{0-\infty}$ was 1870 hr*ng/mL.

After a single oral dose of 20 mg grapiprant tablet, Formulation A29, to Group 3 dogs, the mean $T_{max}$ was 0.891 hours, the mean terminal half-life was 2.17 hours, the mean $C_{max}$ was 1200 ng/ml, and the mean $AUC_{0-\infty}$ was 2340 hr*ng/ml. After a single oral dose of 20 mg grapiprant tablet, Formulation A34, to Group 4 dogs, the mean $T_{max}$ was 0.995 hours, the mean terminal half-life was 8.58 hours, the mean $C_{max}$ was 887 ng/ml, and the mean $AUC_{0-\infty}$ was 2320 hr*ng/mL. After a single oral dose of 20 mg grapiprant tablet, Formulation A31, to Group 5 dogs, the mean $T_{max}$ was 1.40 hours, the mean terminal half-life was 5.87 hours, the mean $C_{max}$ was 697 ng/ml, and the mean $AUC_{0-\infty}$ was 1860 hr*ng/ml. After a single oral dose of 20 mg grapiprant tablet, Batch 120322-1, to Group 6 dogs, the mean $T_{max}$ was 1.09 hours, the mean terminal half-life was 7.52 hours, the mean $C_{max}$ was 816 ng/ml, and the mean $AUC_{0-\infty}$ was 2560 hr*ng/ml.

Mean $T_{max}$ was the shortest after dogs were administered grapiprant suspension, and $AUC_{0-\infty}$ was lowest following a grapiprant capsule. Mean $t_{1/2}$ was the shortest, but $C_{max}$ was highest after a tablet (Formulation A29). Mean $t_{1/2}$ was the longest after a tablet (Formulation A34). Mean $T_{max}$ was the longest, but $C_{max}$ was lowest after a tablet (Formulation A31).

Figure 7:
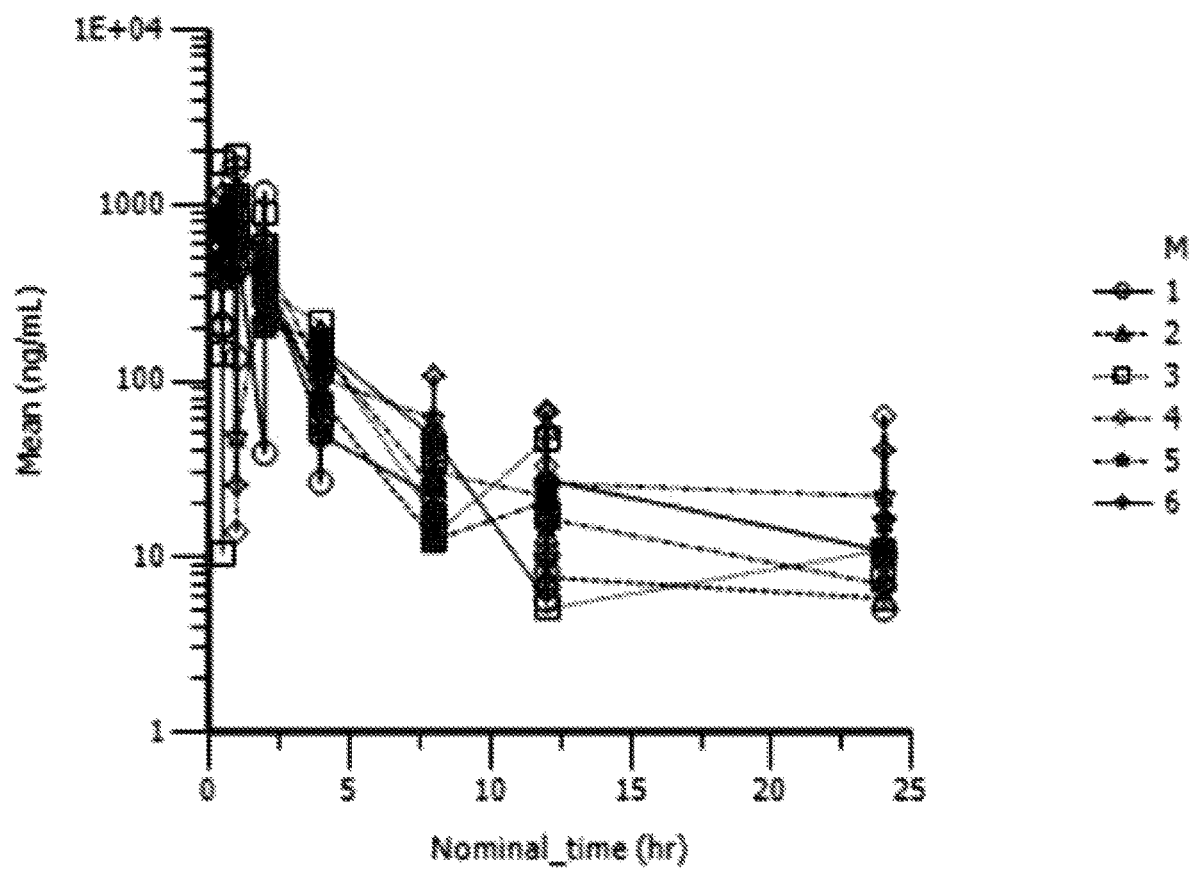
FIG. 7 depicts the combined individual serum concentrations for grapiprant over time for Groups 1-6 dogs, as described in Example 3 and individually shown in FIGS. 1-6.

When normalized for dose received, the $C_{max}$ and $AUC_{0-\infty}$ were similar among groups with only slightly lower absorption ($C_{max}$ and $AUC_{0-\infty}$) in the capsule (Group 1), suspension (Group 2) and the Group 5 tablet formulations; however, analysis of variance (ANOVA) indicated that there was no significant difference among the groups for $C_{max}$, $T_{max}$ and $AUC_{0-\infty}$. FIGS. 1-6 depict the individual serum concentrations of grapiprant over time for Group 1-6 dogs, respectively. FIG. 7 depicts the combined individual serum concentrations for grapiprant over time for Groups 1-6 dogs.

After a single nominal 2-mg/kg oral dose of grapiprant using either a capsule, methylcellulose suspension, or one of four different formulated tablets, pharmacokinetic parameters varied with dose form. When normalized for dose received, the $C_{max}$ and $AUC_{0-\infty}$ were similar among groups with only slightly lower absorption ($C_{max}$ and $AUC_{0-\infty}$) in the capsule (Group 1), suspension (Group 2) and the Group 5 tablet formulations; however, ANOVA indicated no significant difference among the groups for $C_{max}$, $T_{max}$ and $AUC_{0-\infty}$.

Example 4—Further Pharmacokinetic Studies of Grapiprant in Dogs

The objective of this study is to determine the pharmacokinetic profile of several tablet formulations of grapiprant administered to male and female beagle dogs. The test article was tested in four formulations: Group 1 (Formulation A34), Group 2 (Formulation A27), Group 3 (Formulation A29), and Group 4 (Formulation A31), as described above at Table 4 of Example 2. Each tablet formulation of the test article contained 20 mg of the active pharmaceutical ingredient in a distinct excipient mixture. The test article was used without correction for purity or salt content. A single oral dose with one whole tablet was given to dogs as shown below in Table 7.

TABLE 7

Formulations used in this study.

| Group | Number of Animals | Formulation | Nominal Dose Level (mg/kg)* |
|---|---|---|---|
| 1 | 4/4 | 20 mg tablet, Formulation A34 | 2 |
| 2 | 4/4 | 20 mg tablet, Formulation A27 | 2 |
| 3 | 4/4 | 20 mg tablet, Formulation A29 | 2 |
| 4 | 4/4 | 20 mg tablet, Formulation A31 | 2 |

*Based on animal bodyweight of 10 kg.

Animals received a detailed clinical evaluation before inclusion/randomization on Day −6. Animal bodyweights were within normal limits for beagles of this age and gender. After dosing, no signs of regurgitation or vomit were observed. Dogs were dosed with a nominal 2-mg/kg oral dose of grapiprant using four different formulated tablets.

The actual dose levels for Group 1 ranged from 2.05 to 3.23 mg/kg, Group 2 ranged from 1.82 to 3.15 mg/kg, Group 3 ranged from 1.69 to 3.23 mg/kg, and Group 4 ranged from 2.05 to 3.15 mg/kg. After a single oral dose of 20-mg grapiprant tablet Formulation A34 to Group 1 dogs, the mean $T_{max}$ was 0.975 to 0.992 hour. The mean terminal half-life was 5.71 to 6.88 hours. Mean $C_{max}$ was 1750 to 2180 ng/mL, and mean $AUC_{0-\infty}$ was 4420 to 4650 hr*ng/mL. After a single oral dose of 20-mg grapiprant tablet Formulation A27 to Group 2 dogs, the mean $T_{max}$ was 0.704 to 0.709 hours. The mean terminal half-life was 6.41 to 9.22 hours. Mean $C_{max}$ was 1430 to 2460 ng/mL, and mean $AUC_{0-\infty}$ was 3190 to 5160 hr*ng/mL. After a single oral dose of 20-mg grapiprant tablet Formulation A29 to Group 3 dogs, the mean $T_{max}$ was 0.704 to 0.933 hours. The mean terminal half-life was 3.11 to 6.83 hours. Mean $C_{max}$ was 1270 to 1900 ng/mL, and mean $AUC_{0-\infty}$ was 2840 to 3530 hr*ng/mL. After a single oral dose of 20 mg grapiprant tablet Formulation A31 to Group 4 dogs, the mean $T_{max}$ was 0.817 to 0.933 hour. The mean terminal half-life was 5.15 to 7.42 hours. Mean $C_{max}$ was 1430 to 2160 ng/mL, and mean $AUC_{0-\infty}$ was 2860 to 3410 hr*ng/mL.

Figure 8:
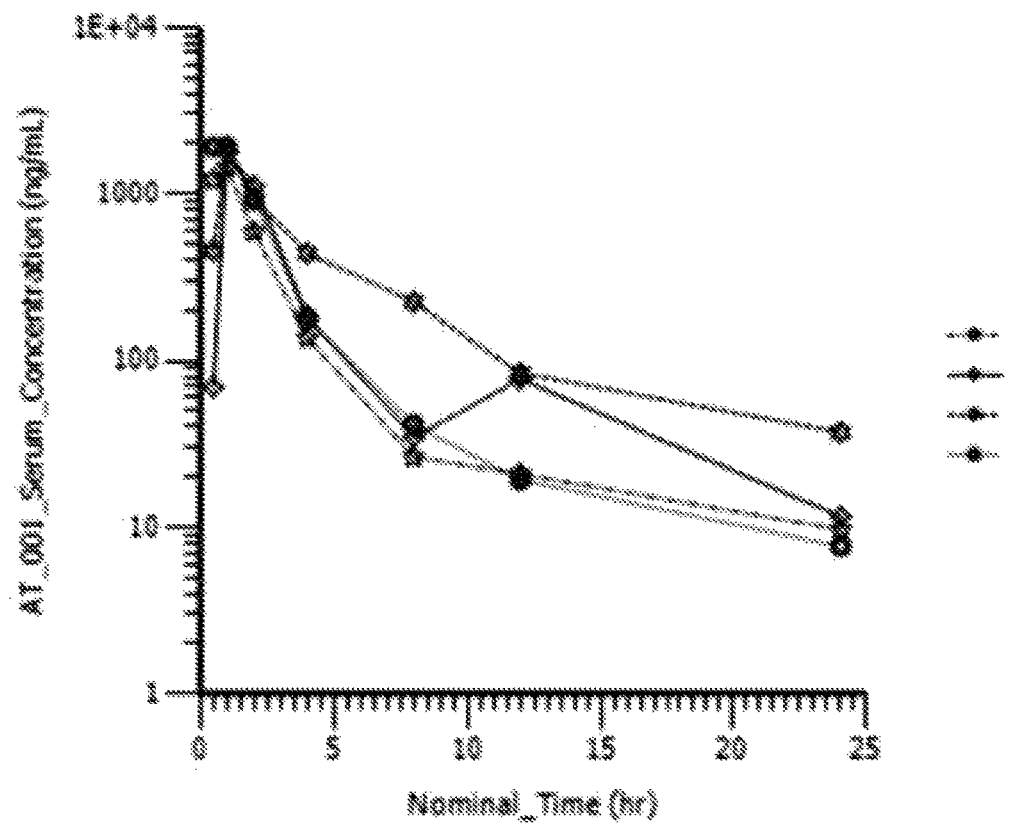
FIG. 8 depicts individual serum concentrations of grapiprant over time for Group 1 male dogs tested with Formulation A34, as described in Example 4.
Figure 9:
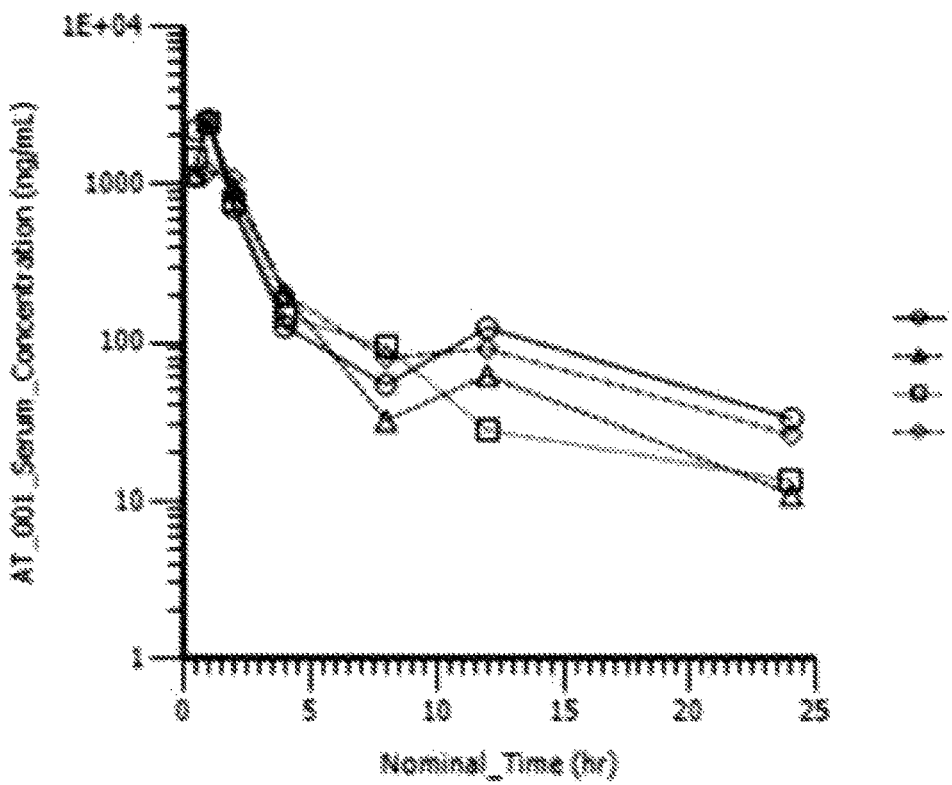
FIG. 9 depicts individual serum concentrations of grapiprant over time for Group 1 female dogs tested with Formulation A34, as described in Example 4.
Figure 10:
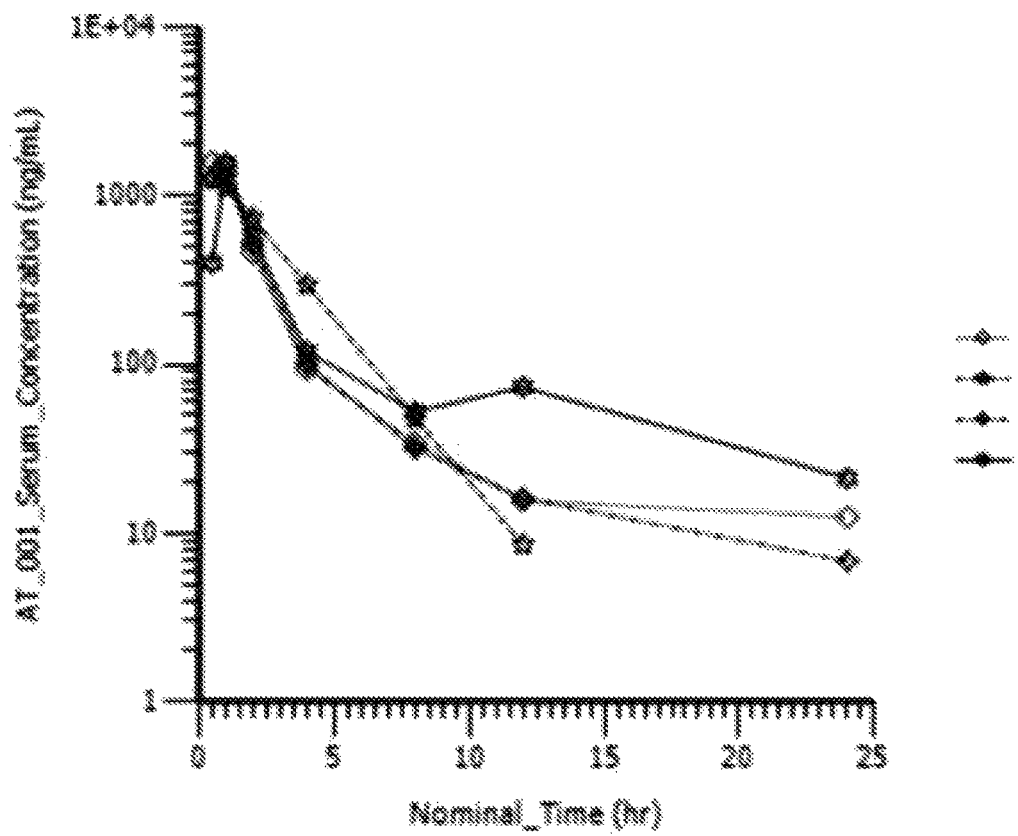
FIG. 10 depicts individual serum concentrations of grapiprant over time for Group 2 male dogs tested with Formulation A27, as described in Example 4.
Figure 11:
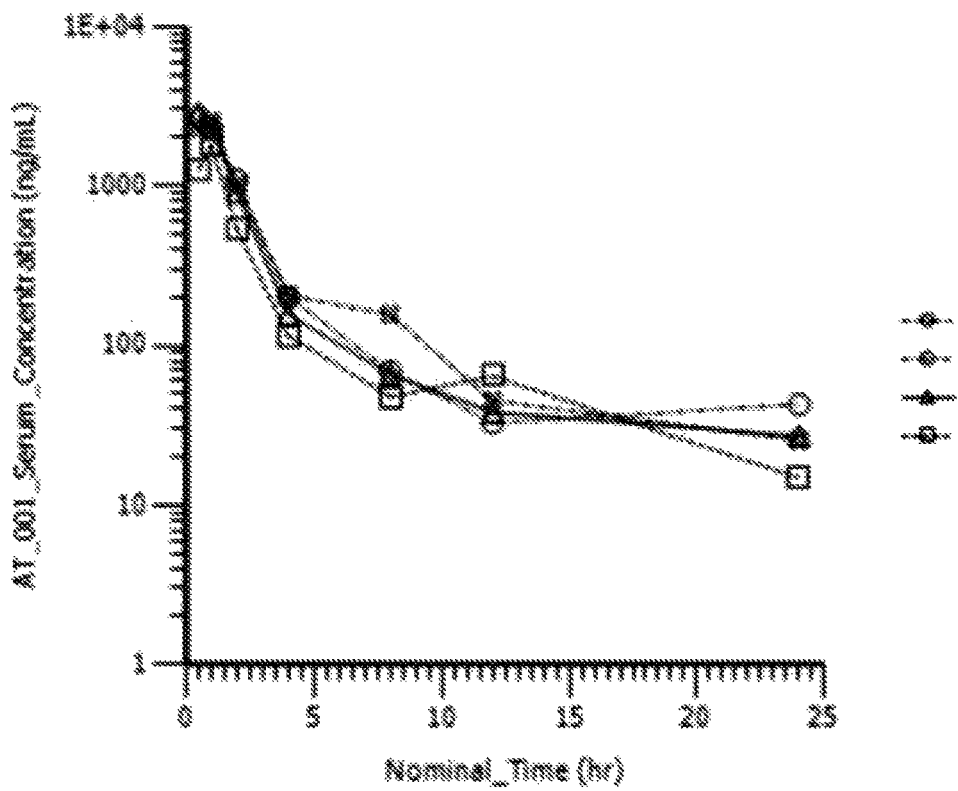
FIG. 11 depicts individual serum concentrations of grapiprant over time for Group 2 female dogs tested with Formulation A27, as described in Example 4.
Figure 12:
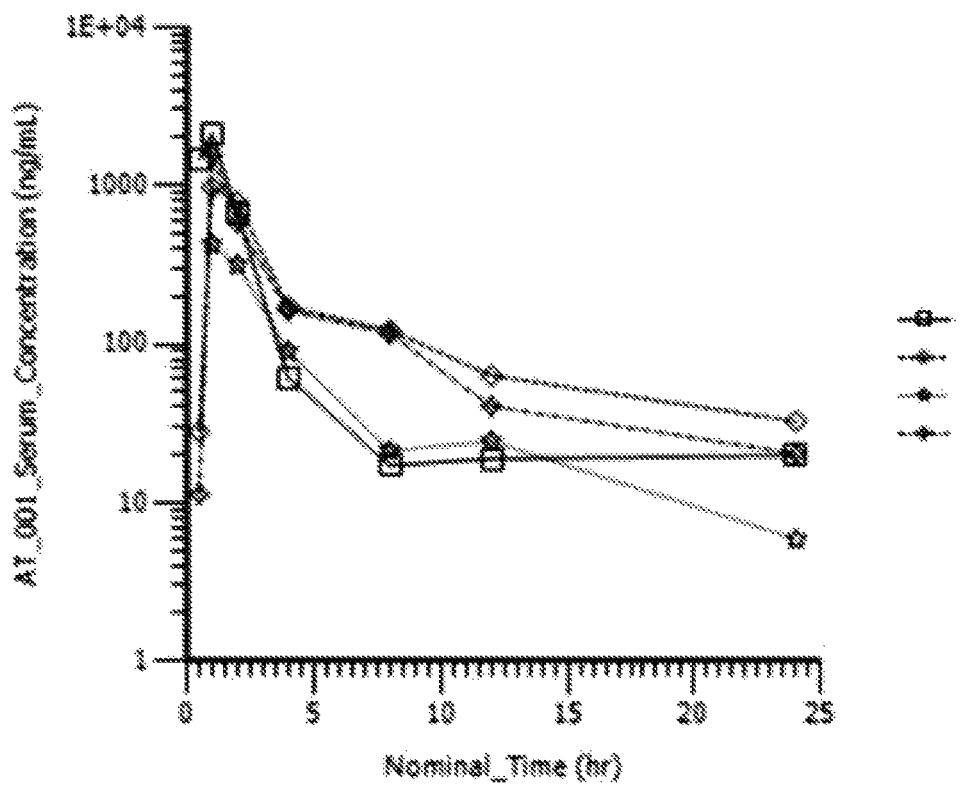
FIG. 12 depicts individual serum concentrations of grapiprant over time for Group 3 male dogs tested with Formulation A29, as described in Example 4.
Figure 13:
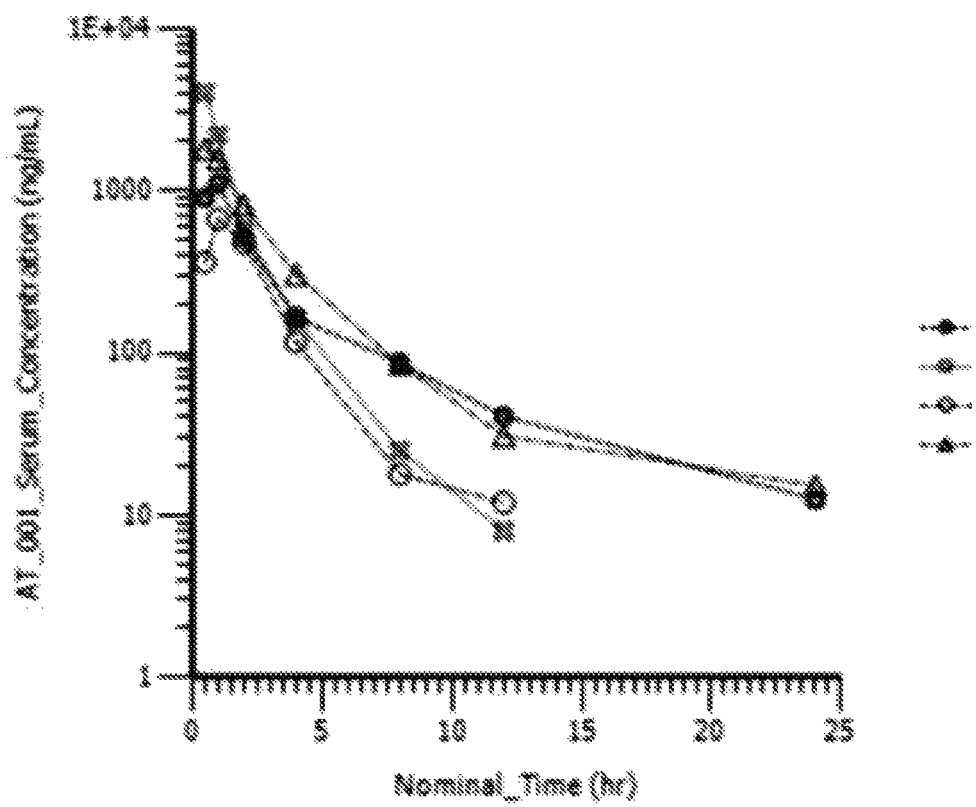
FIG. 13 depicts individual serum concentrations of grapiprant over time for Group 3 female dogs tested with Formulation A29, as described in Example 4.
Figure 14:
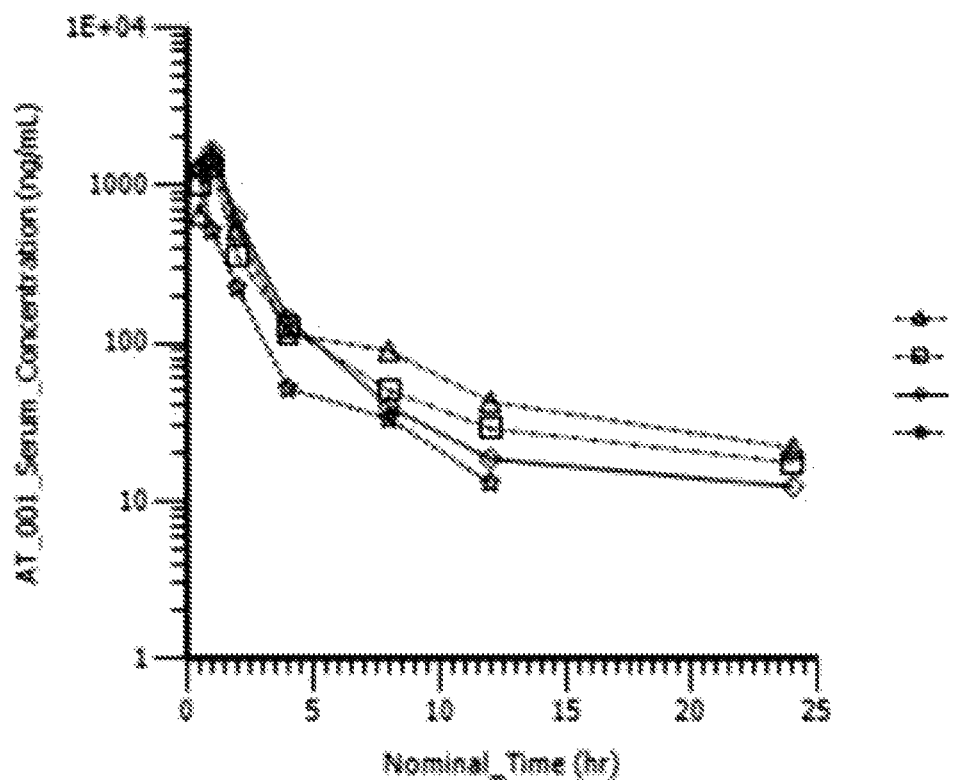
FIG. 14 depicts individual serum concentrations of grapiprant over time for Group 4 male dogs tested with Formulation A31, as described in Example 4.
Figure 15:
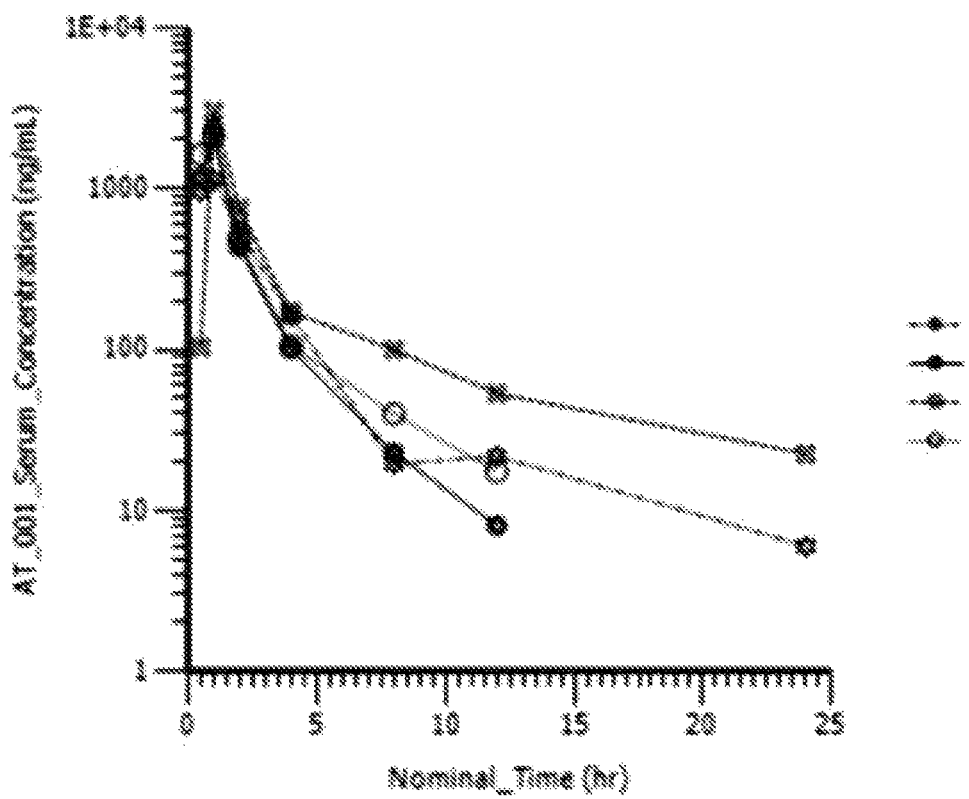
FIG. 15 depicts individual serum concentrations of grapiprant over time for Group 4 female dogs tested with Formulation A31, as described in Example 4.

FIGS. 8 and 9 depict individual serum concentrations of grapiprant over time for Group 1 male and female dogs, respectively, tested with Formulation A34. FIGS. 10 and 11 depict individual serum concentrations of grapiprant over time for Group 2 male and female dogs, respectively, tested with Formulation A27. FIGS. 12 and 13 depict individual serum concentrations of grapiprant over time for Group 3 male and female dogs, respectively, tested with Formulation A29. FIGS. 14 and 15 depict individual serum concentrations of grapiprant over time for Group 4 male and female dogs, respectively, tested with Formulation A31.

Figure 16:
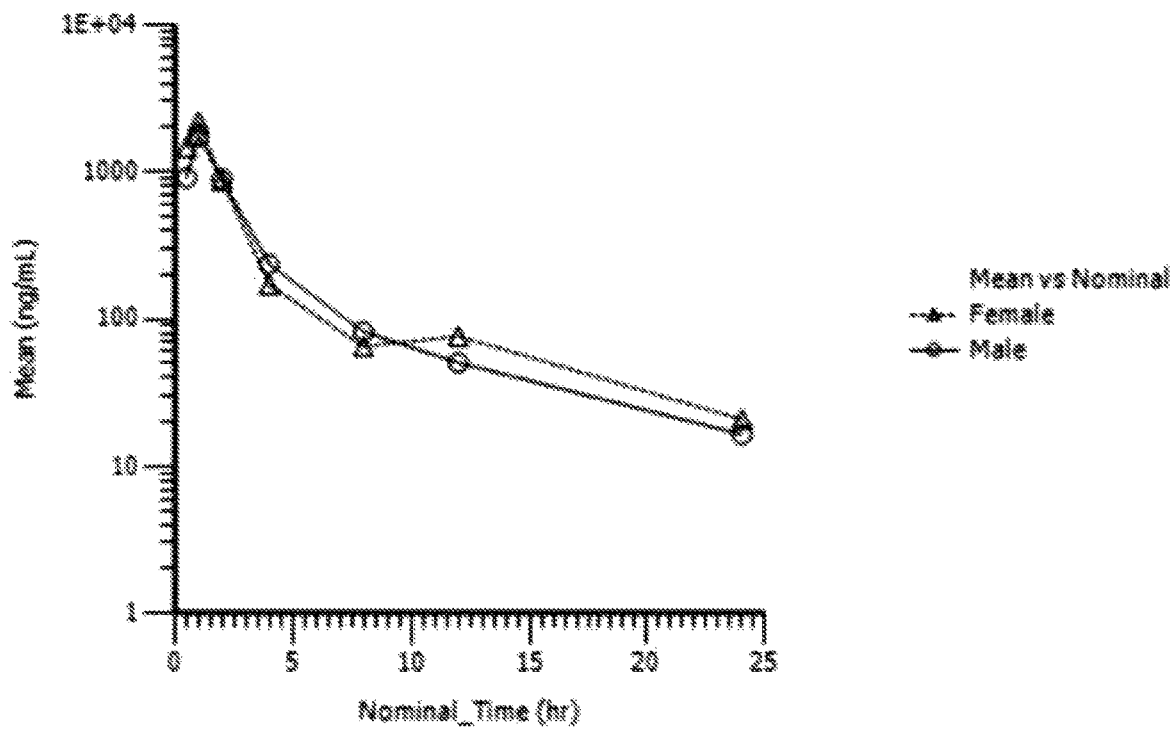
FIG. 16 depicts the mean serum concentrations of grapiprant over time for Group 1 dogs grouped by male and female, as described in Example 4 and individually shown at FIGS. 8 and 9.
Figure 17:
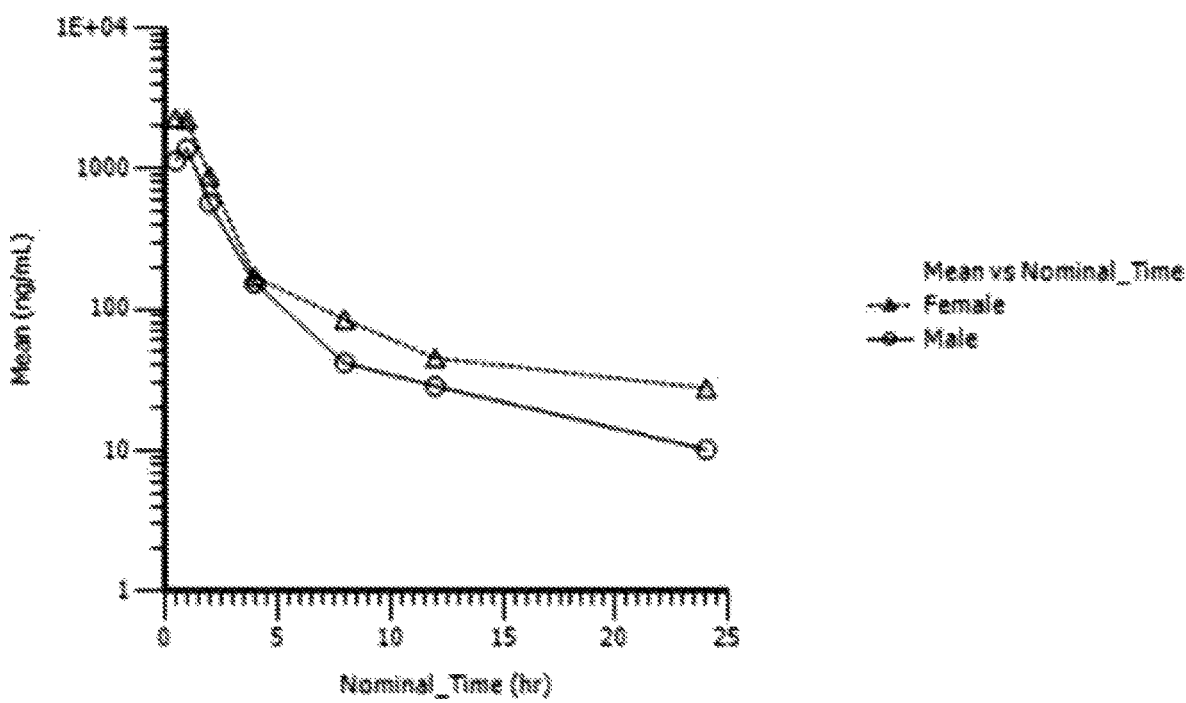
FIG. 17 depicts the mean serum concentrations of grapiprant over time for Group 2 dogs grouped by male and female, as described in Example 4 and individually shown at FIGS. 10 and 11.
Figure 18:
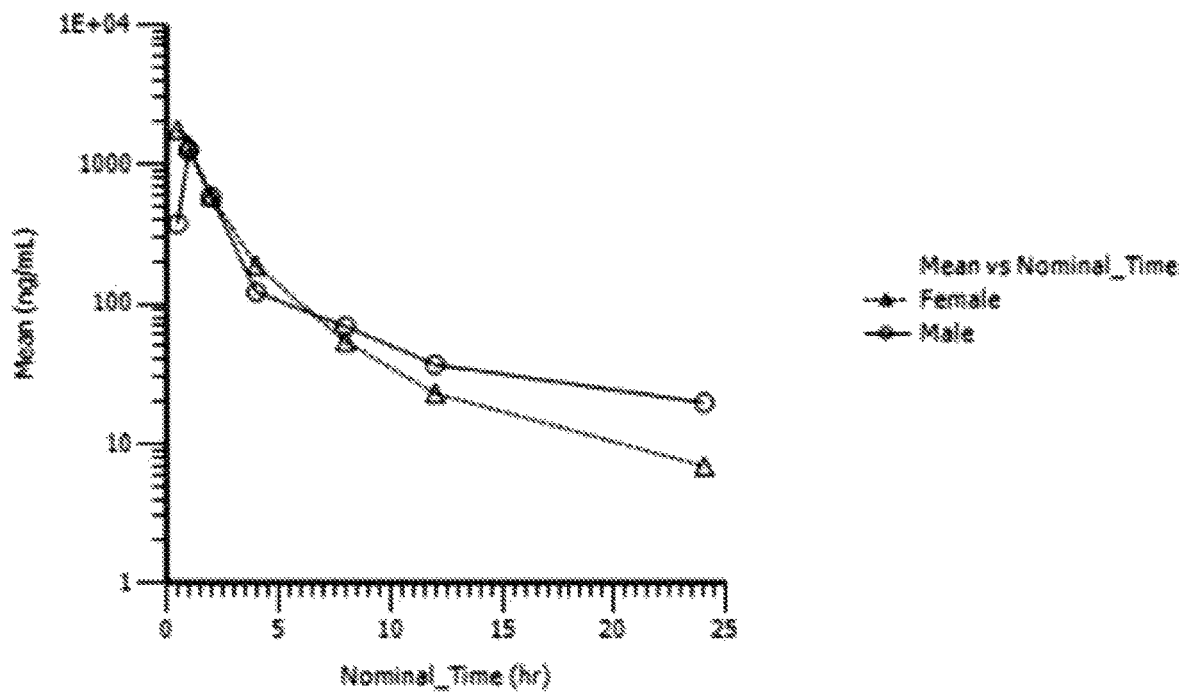
FIG. 18 depicts the mean serum concentrations of grapiprant over time for Group 3 dogs grouped by male and female, as described in Example 4 and individually shown at FIGS. 12 and 13.
Figure 19:
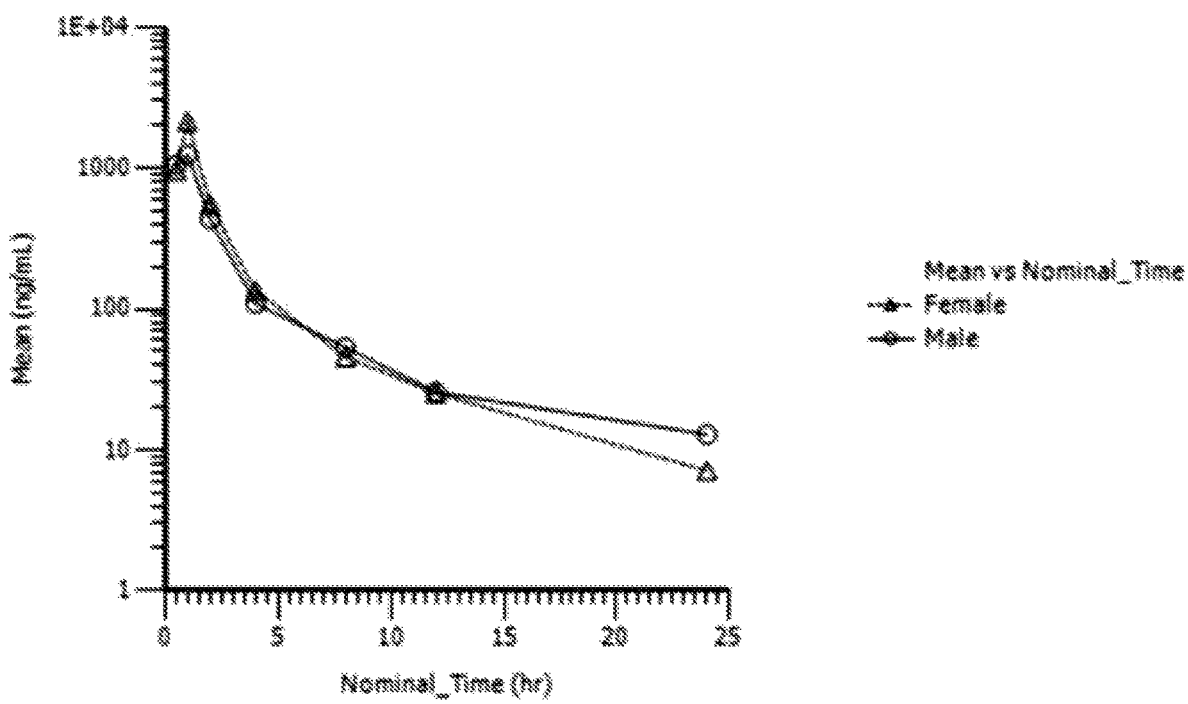
FIG. 19 depicts the mean serum concentrations of grapiprant over time for Group 4 dogs grouped by male and female, as described in Example 4 and individually shown at FIGS. 14 and 15.
Figure 20:
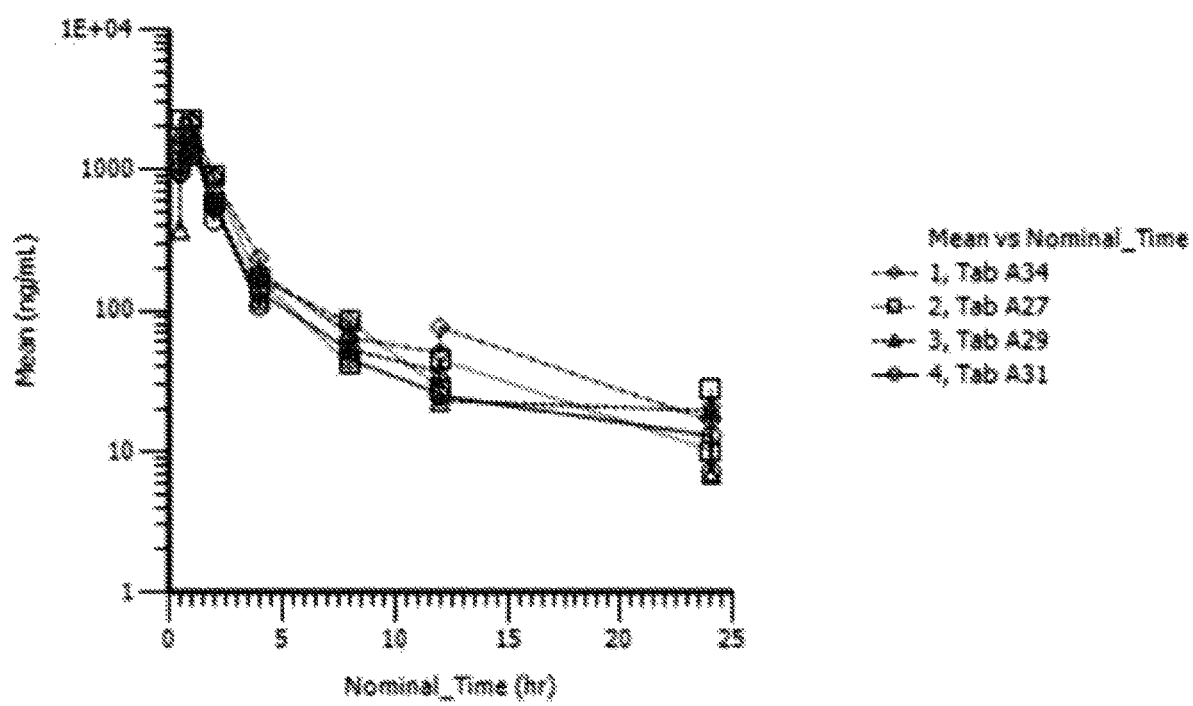
FIG. 20 depicts the mean serum concentrations of grapiprant over time for Groups 1-4 dogs, as described in Example 4 and shown variously above at FIGS. 8-19.

FIG. 16 depicts the mean serum concentrations of grapiprant over time for Group 1 dogs grouped by male and female, as individually shown at FIGS. 8 and 9. FIG. 17 depicts the mean serum concentrations of grapiprant over time for Group 2 dogs grouped by male and female, as individually shown at FIGS. 10 and 11. FIG. 18 depicts the mean serum concentrations of grapiprant over time for Group 3 dogs grouped by male and female, as individually shown at FIGS. 12 and 13. FIG. 19 depicts the mean serum concentrations of grapiprant over time for Group 4 dogs grouped by male and female, as described individually shown at FIGS. 14 and 15. FIG. 20 depicts the mean serum concentrations of grapiprant over time for Groups 1-4 dogs, as shown at FIGS. 8-19.

No sex difference was observed for any tablet formulation in the study. Mean $T_{max}$ was the longest and variability for AUC was the lowest after a single oral dose of 20 mg grapiprant tablet Formulation A34. Mean $T_{max}$ was the shortest and $t_{1/2}$ was the longest and variability for $C_{max}$ was the lowest after a tablet Formulation A27. Tablet Formulation A29 had the lowest mean $C_{max}$ and $t_{1/2}$, but had the highest variability for $C_{max}$ and AUC values. Overall, all four formulations were very similar.

Following a single nominal 2-mg/kg oral dose of grapiprant using four different formulated tablets, $C_{max}$ among formulations did not differ significantly (p>0.05), but $T_{max}$ was significantly different (p<0.05). $T_{max}$ of tablet Formulation A34 was significantly longer than that of tablet Formulations A27, A29, and A31 (p<0.05), no other pair comparisons differed significantly (p>0.05). $AUC_{last}$ of any tablet formulation did not differ significantly from others when pair comparisons were done (p>0.05).

Example 5—Efficacy Study of Grapiprant in Cats

The objective of this pilot study was to validate that this model/pain scoring system can differentiate positive from negative control animals in controlling the pain and inflammation of onychectomy and to test the effectiveness of a single dose of grapiprant in controlling the pain and inflammation associated with onychectomy in cats.

Following an acclimation period of 7, 8, or 9 days, a total of 30 adult cats were randomly divided between three treatment groups with ten animals assigned to each group. All animals were randomly assigned to a given surgery day such that within each day, an equal number of cats was from each treatment group. Within each day, the order of surgery was also randomized. On Day 0, all study animals were administered a subcutaneous injection of butorphanol at a target dose of 0.4 mg/kg bodyweight just prior to treatment administration preceding surgery.

All animals in Group 1 were orally-administered a 6 mg tablet of Positive Control (Onsior™, robenacoxib), animals in Group 2 were administered an empty gelatin capsule as the Negative Control, and animals in Group 3 were administered a 20 mg tablet of grapiprant (Formulation A34, see Table 4 in Example 2 above) all about 30 minutes before onychectomy. A water chaser was not administered following dosing. On Days 1 and 2, animals in Group 1 were administered a 6 mg tablet or Positive Control, while animals in Groups 2 and 3 were administered an empty gelatin capsule. Details of the experimental study design are summarized in Table 8.

TABLE 8

Description of Study Design.

| Group | Number of Animals | Dose | Route | Dose |
|---|---|---|---|---|
| 1 | 10 | Positive Control (Onsior ™) | PO | Days 0, 1, and 2: 6 mg/animal (full 6 mg tablet) |
| 2 | 10 | Negative Control (gelatin capsule) | PO | Days 0, 1, and 2: 0 mg (empty capsule) |
| 3 | 10 | Grapiprant (20 mg tablet) Formulation A34 | PO | Days 0: ~20 mg/animal (full 20 mg tablet) Days 1 and 2: 0 mg (empty capsule) |

The variables evaluated and the intervals they were determined are summarized in Table 9.

TABLE 9

Variables Evaluated and Description of Study Design.

| Study Day | Activity/Parameter |
|---|---|
| Throughout | General health observations (at least once per day) |
| Up to Days −9 to −1 | Acclimation |
| Day −4 | Physical Examinations |
| Day −1 | Body Weight Measurements |
| Day −1 | Randomization |
| Day 0 (0.5 hours, 1 hour, and every other hour until animal received two consecutive scores of one) | Sedation Score |
| Days 0 (0.5, 1, 3, 5, and 8 hours-post extubation), 1 (24 hours post-dose Day 0, 1200 to 1400, and 1700 to 1900), 2 (48 hours post-dose Day 0, 1200 to 1400, and 1700 to 1900), and 3 (72 hours post-dose Day 0) | Analgesia Scoring |

On Day 0, cats were orally-dosed with the Positive Control (Group 1), Negative Control (Group 2), or grapiprant (Group 3) about 30 minutes before onychectomy. On Days 1 and 2, animals in Group 1 were orally dosed with Positive Control while animals in Groups 2 and 3 were given the Negative control.

Surgical Procedure. Surgeries for the study were staggered over different days. Study animals were divided into sequences of 9, 9, and 12 cats to allow for surgeries to be performed over three days. The day of surgery was considered to be Day 0 for that sequence. All animals were given a subcutaneous injection of butorphanol at a target dose of 0.4 mg/kg bodyweight just before treatment administration preceding surgery. Cats were premedicated with acepromazine (target 0.05 mg/kg, subcutaneous) and anesthesia was induced with propofol (not more than 8 mg/kg, intravenous slowly to effect). Anesthesia was maintained by isoflourane (0.5 to 5% in 100% oxygen). Animals were intubated at the discretion of veterinary staff. During surgical procedures, each animal was monitored for at least heart rate and respiratory rate. Onychectomy of the front paws on all animals was performed with surgical scalpel and soft tissues and skin were closed with GLUture™ Topical Tissue Adhesive at the conclusion of surgery. Following surgery, each animal was periodically monitored until full recovery. Each cat was extubated when the swallowing reflex was observed to return. Extubation time (time zero=$T_0$) was recorded as the end of surgery.

All study animals were scored for sedation and analgesia the following schedule in Table 10.

TABLE 10

Sedation and analgesia scoring schedule.

| Day | Time | Assessment | Comments |
|---|---|---|---|
| 0 | 0 | Extubation | |
| | 30 ± 10 min | Sedation score | Performed by masked |
| | | Analgesia score | Assessor |
| | 1 hour ± 10 min | Sedation score | As above |
| | | Analgesia score | |
| | 3 hour ± 30 min | Sedation score (or until animal received two consecutive scores of 1) | As above |
| | | Analgesia score | |
| | 5 hour ± 30 min | Sedation score (or until animal received two consecutive scores of 1) | As above |
| | 8 hour ± 30 min | Sedation score (or until animal received two consecutive scores of 1) | As above |
| | 12 hour ± 30 min | Analgesia score | As above |
| | 16 hour ± 30 min | Analgesia score | As above |
| | 20 hour ± 30 min | Analgesia score | As above |
| | 24 hour ± 30 min | Analgesia score | As above |
| 1 | 24 hour ± 1 hour (post-Day 0) | Analgesia score | As above |
| | Mid-day 1200-1400 hours | Analgesia score | As above |
| | Early evening 1700-1900 hours | Analgesia score | As above |
| 2 | 4 hour ± 1 hour (post-Day 0) | Analgesia score | As above |
| | Mid-day 1200-1400 hours | Analgesia score | As above |
| | Early evening 1700-1900 hours | Analgesia score | As above |
| 3 | 72 hour ± 1 hour (post-Day 0) | Analgesia score | As above |

Each study animal was observed and given a sedation score at specified time points during the study or until the animal received two consecutive scores of 1. A five-point scoring system was used to score sedation post-operatively.

Analgesia scores were given at specified time points during the study. The masked assessor observed the cat in its cage and then gently palpated the surgical site to assess pain. Analgesia was scored by the same assessor during the first 8 hours of the study. Observations after 8 hours were made by alternative assessors, as necessary.

Results. The cat was evaluated as the experimental unit. Differences between treatment groups were evaluated at alpha of 0.05. Sedations and analgesia scores were evaluated using methods appropriate for ordinal data measured repeatedly over time, such as the GLIMMIX procedure (SAS Institute, Cary, NC, version 9.3). A multinomial distribution was assumed and a cumulative logit link used. The model included treatment group, time, and the group by time interaction as fixed effects. Given the unequal spacing of the time intervals, a compound symmetric (CS) or heterogeneous CS structure was assumed for the covariance matrix, depending on the Akaike's Information Criterion. If the group by time interaction was significant, within time comparisons were made, comparing groups in a pairwise fashion. If the interaction was not significant, the main effect of group was evaluated. If the main effect of group was significant, pairwise comparisons among groups were made. If the algorithm used in the model fitting process did not converge, alternative models were evaluated. Mean values are used to summarize the results. Additionally, each cat was categorized as either a success or failure based on the need for pain intervention. The percent of successes within treatment groups was evaluated using methods appropriate for binary outcomes, assuming a binomial distribution and logit link. The model included treatment group as a fixed effect.

If the effect of treatment was significant, pairwise comparisons between groups were made. The percent failure within group and 95% confidence intervals are presented. Intervention results were also evaluated using methods appropriate for binary data measured repeatedly over time. A binomial distribution was assumed and a logit link used.

All animals were successfully dosed the specified test formulation on Day 0 with the Positive Control, Negative Control, and grapiprant formulation. Beginning at the one hour time point following the surgical intervention and continuing for the duration of the observation period (72 hours), animals in the Negative Control group consistently had higher analgesia scores than their counterparts in the Positive Control and grapiprant groups. However, this trend only reached statistical significance at the Day 1 mid-day time point ($P<0.05$). These findings were also found when three animals with non-treatment related extremity findings (swollen paws and trauma to paw) were excluded from the analysis, but the differences did not achieve statistical significance at any time point. The animals in the placebo group required more frequent, and a greater total number of "rescue" analgesia (butorphanol) than those in either of the other two groups, although these differences were not statistically significant.

In summary, administration of the test article grapiprant was associated with decreased analgesia scores (reduced pain), without an apparent effect on sedation scores when compared to placebo controls. These relationships were similar to those found for the Positive Control treatment.

Example 6—Grapiprant Oral Tablet for Treating Osteoarthritis in Dogs

In a masked, multi-centered dose ranging field study, dogs with naturally occurring osteoarthritis were treated with grapiprant at 2 mg/kg once daily (SID), 5 mg/kg once daily, 4 mg/kg twice daily (BID), or placebo twice daily to assess the control of pain and inflammation. Dogs were randomly assigned to one of the four treatment groups and treated orally with Formulation A34 tablets of 20, 60, and 100 mg, or placebo tablets (matched to the 4 mg/kg group). (See above at Example 2, Table 4). The control of pain and inflammation was assessed by the owner using the validated Canine Brief Pain Inventory (CBPI) assessment tool, which consists of a pain severity score (PSS), a Pain Interference Score (PIS), and an Owner Impression of dog's quality of life. CBPI scoring, as well as a veterinarian assessment of osteoarthritis, were conducted at Study Day 0 (baseline) and Days 7, 14, 21, and 28.

In total 476 dogs were screened in the study with 108 screen failures, resulting in 336 dogs in the per protocol population. Table 11 lists the number of animals from each group in the per protocol population.

TABLE 11

Study population numbers per treatment group.

| Treatment Group | Per Protocol Population |
| --- | --- |
| Placebo | 83 |
| 2 mg/kg SID | 86 |
| 5 mg/kg SID | 82 |
| 4 mg/kg BID | 85 |

There was no difference in median PSS or PIS scores among the groups at baseline. A positive response (decreases in the PSS and PIS scores) was observed in all treatment groups with statistically significant differences seen in the 2 and 5 mg/kg SID groups compared to placebo. On Days 14, 21, and 28, the PSS scores differed significantly ($p \leq 0.05$) among groups, with statistically significant greater improvements for the 2 mg/kg SID group in pairwise comparisons to placebo on Days 14 and 28, and on Days 14, 21, and 28 for the 5 mg/kg group. For the PIS scores, the groups differed significantly ($p \leq 0.05$) on Day 28 with statistically significant greater improvements for the 2 and 5 mg/kg SID groups in pairwise comparisons to placebo. The descriptive statistics for the PSS and PIS scores from the CBPI are given in Tables 12 and 13.

The dose groups had similar efficacy with no benefit from increasing the dose, as shown in the descriptive statistics from the PSS and PIS scores from the CBPI (Tables 12 and 13). The median decreases from baseline PSS scores were 48, 48.53, and 44.44 for the 2 mg/kg SID, the 5 mg/kg SID, and the 4 mg/kg BID dose groups, respectively, compared to only 28 for the placebo group. For the PIS scores, the median decreases from baseline were 53.25, 55.27, and 52.27 for the 2 mg/kg SID, the 5 mg/kg SID, and the 4 mg/kg BID dose groups, respectively, compared to only 39.13 for the placebo group. These data suggest that the 2 and 5 mg/kg SID doses were both effective and that twice daily dosing added no benefit.

TABLE 12

Pain Severity Scores (PSS) descriptive statistics.

| Study Day | | Placebo | 2 mg/kg SID | 4 mg/kg BID | 5 mg/kg SID | p-value* |
| --- | --- | --- | --- | --- | --- | --- |
| Day 0 | N | 83 | 86 | 85 | 82 | 0.5217 |
| | Median | 5.00 | 5.25 | 5.25 | 5.00 | (r) |
| | p-value+ | | 0.9902 | 0.9999 | 0.5325 | |
| % Change*: Day 7 | N | 79 | 84 | 83 | 81 | 0.1024 |
| | Median | −14.29 | −24.26 | −17.39 | −22.22 | (r) |
| | p-value+ | | 0.0719 | 0.9452 | 0.2785 | |
| % Change*: Day 14 | N | 81 | 85 | 80 | 81 | 0.0441 |
| | Median | −22.22 | −32.00 | −28.29 | −30.00 | (r) |
| | p-value+ | | 0.0380 | 0.1739 | 0.0370 | |
| % Change*: Day 21 | N | 75 | 81 | 77 | 77 | 0.0478 |
| | Median | −25.93 | −35.00 | −38.89 | −44.44 | (r) |
| | p-value+ | | 0.1260 | 0.1102 | 0.0207 | |
| % Change*: Day 28 | N | 77 | 84 | 75 | 78 | 0.0109 |
| | Median | −28.00 | −48.00 | −44.44 | −48.53 | (r) |
| | p-value+ | | 0.0250 | 0.1028 | 0.0048 | |

*Overall p-values generated by analysis of variance with terms for treatment, site and treatment by site interaction;
+Pairwise comparisons to Placebo;
**Percent Change from Day 0

TABLE 13

Pain Interference Score (PIS) descriptive statistics

| Study Day | | Placebo | 2 mg/kg SID | 4 mg/kg BID | 5 mg/kg SID | p-value* |
| --- | --- | --- | --- | --- | --- | --- |
| Day 0 | N | 83 | 86 | 85 | 82 | 0.5434 |
| | Median | 5.67 | 6.00 | 5.83 | 5.50 | (r) |
| | p-value+ | | 0.7963 | 0.9902 | 0.3876 | |
| % Change**: Day 7 | N | 79 | 84 | 83 | 81 | 0.3295 |
| | Median | −15.91 | −27.97 | −28.57 | −26.92 | (r) |
| | p-value+ | | 0.3039 | 0.4652 | 0.1953 | |
| % Change**: Day 14 | N | 81 | 85 | 80 | 81 | 0.2033 |
| | Median | −27.45 | −33.33 | −35.24 | −40.00 | (r) |
| | p-value+ | | 0.2817 | 0.3693 | 0.0836 | |
| % Change**: Day 21 | N | 75 | 81 | 77 | 77 | 0.1166 |
| | Median | −35.71 | −47.83 | −42.11 | −53.85 | (r) |
| | p-value+ | | 0.1777 | 0.2755 | 0.0541 | |
| % | N | 77 | 84 | 75 | 78 | 0.0321 |

TABLE 13-continued

| | Pain Interference Score (PIS) descriptive statistics | | | | |
|---|---|---|---|---|---|
| Study Day | | Placebo | 2 mg/kg SID | 4 mg/kg BID | 5 mg/kg SID | p-value* |
| Change**: Day 28 | Median p-value+ | −39.13 | −53.25 0.0416 | −52.27 0.1146 | −55.27 0.0195 | (r) |

*Overall p-values generated by analysis of variance with terms for treatment, site and treatment by site interaction;
+Pairwise comparisons to Placebo;
**Percent Change from Day 0

Based on the results of the PSS and PIS scores of the CBPI, the 2 mg/kg SID and the 5 mg/kg SID dose are equally effective in controlling the pain and inflammation of osteoarthritis in dogs. The preliminary estimated mean effective canine dose of 2 mg/kg SID based on preliminary extrapolation calculations from pharmacokinetic/pharmacodynamic studies in human Phase 1 and 2 trials, protein binding, and comparative receptor affinity of grapiprant between humans and dogs, was confirmed in the dose ranging field study. The dose was effective in field conditions of use without food restrictions. Thus, these results support the use of 2 mg/kg SID given with or without food for the control of pain and inflammation associated with osteoarthritis in dogs.

Example 7—9-Month Oral Toxicity Study of Grapiprant in Dogs with 4-Week Recovery (06NG032)

Grapiprant was administered orally, once daily, for nine consecutive months to Beagle dogs at doses of 0 (0.5% methylcellulose), 1, 6, and 50 mg/kg/day in a dose volume of 5 mL/kg. Four animals per sex were used in each dose group and two additional animals per sex in the 50 mg/kg dose group for recovery purposes. Clinical signs and food consumption were assessed daily. Bodyweight was recorded weekly. Ophthalmologic examination was performed on Weeks 20 and 38 of the dosing phase and Week 4 of the recovery phase. Electrocardiograms were recorded on Weeks 13, 26, and 38 of the dosing phase and Week 4 of the recovery phase. Hematology, coagulation, and serum chemistry parameters were monitored on Weeks 13, 26, and 39 of the dosing phase and Week 4 or 5 of the recovery phase. Urinalyses were performed on Week 37 of the dosing phase and Week 3 or 4 of the recovery phase. Serum drug concentrations of grapiprant were measured at 0.5, 1, 2, 4, 8, and 24 hours post-dose on Day 1 (50 mg/kg only) and at Week 38. At the end of the dosing or recovery period, dogs were euthanized and necropsied. After gross examination, selected organs were weighed, and a comprehensive set of tissues was collected and processed for microscopic examination.

There were no deaths or drug related effects on bodyweight, food consumption, ophthalmology, electrocardiograms, hematology, coagulation, organ weights, or gross pathological findings up to 50 mg/kg during the 9-month dosing period. Gastrointestinal effects such as loose or mucous stool, which sometimes included slight bloody or red material were observed in all groups including the control. The incidence was higher in some animals at 1-50 mg/kg compared with that in the control animals. A significant decrease in mean serum albumin was observed at Weeks 26 and 39 (up to −14% vs. control value) at 50 mg/kg and in mean albumin/globulin (A/G) ratio at Week 39 at 6 mg/kg (−16%). Individually, there was a dose-related trend for increase in incidence and decrease in onset time, with decreases in albumin (up to −41% vs. pre-study), total protein (up to −30%) and/or calcium (up to −18%). These findings returned to normal range after a one-month reversal. The serum parameter changes were recovered at the end of the recovery period. There were no noteworthy findings during or at the end of the 4-week recovery period.

After single or repeated oral administrations, there were no sex related differences in the systemic exposure to grapiprant, no accumulation of grapiprant was observed after 1, 6, and 50 mg/kg/day dosing regimen. The combined mean systemic exposure to grapiprant increased with dose in the dose range proportionally in the range 1-6 mg/kg/day, more than proportionally in the range 6-50 mg/kg/day. Due to mild regeneration of the mucosal epithelium of the ileum in one male at 50 g/kg, the level with no observed adverse effects was 6 mg/kg. The combined mean $C_{max}$ was 3,480 ng/mL and $AUC_{0\text{-}24}$ was 10,600 at 6 mg/kg. The combined mean $C_{max}$ was 49,283 ng/mL and $AUC_0$-24 was 138,667 ng·h/mL.

There were no drug-related effects on mortality, bodyweight, food consumption, ophthalmology, electrocardiograms, hematology, coagulation, organ weights or gross pathological findings at doses up to 50 mg/kg administered for a 9-month dosing period. Although functional effects such as loose or mucous stool and decreases in total protein, albumin and calcium in serum chemistry were observed at doses above 1 mg/kg, they were secondary gastrointestinal effects caused by the $EP_4$ antagonism and, therefore, not adverse effects of the drug. Meanwhile, histopathological changes of mucosal epithelium in the ileum observed at 50 mg/kg were considered an adverse effect of the drug.

Example 8—Effect of Grapiprant on Lameness and Pain in Dogs (CL-001)

Twenty intact adult female hounds underwent surgical meniscal release of the right stifle and were maintained for at least 8 weeks to allow osteoarthritis to develop. Radiographic signs of osteoarthritis were confirmed in all dogs about 8 weeks post-surgery. Animals were randomized into three groups: negative control (n=6), positive control (n=7) treated with 5 mg/kg firocoxib daily, and grapiprant (n=7) dosed once daily at 30 mg/kg. Dosing was based on baseline bodyweight.

Baseline physical exams, bodyweights, hematology, serum chemistry and urinalysis were obtained on study Day −1 and repeated on Day 13. Orthopedic assessments were conducted on Day −1, Day 2, Day 6, and Day 13, including a kinetics assessment using the GAITRite system to determine left hindlimb: right hindlimb ratios for peak pressure, stride length, step length, and stance time, a 5-point scale lameness evaluation, VAS assessments of right hindlimb function, right stifle pain and effusion, and comfortable range of motion measurements of both stifles using a goniometer.

The groups did not differ significantly for any orthopedic parameter except for lower lameness scores in the grapiprant treated group on Day 2 compared to the negative and positive control groups, and a higher function score (less lameness) in the negative control at baseline compared to positive control and grapiprant treated groups. The grapiprant treated group and the negative control treated group both had statistically significant lower pain scores on Days 2 and 6 compared to baseline. The positive control group improved statistically significant mean peak pressure ratios on Day 13 and in mean lameness and mean function scores on Day 6 and 13 compared to baseline. Grapiprant treated animals showed decreases in mean total protein, albumin, and globulin.

Grapiprant given at 30 mg/kg over 14 days was effective at day 2 in ameliorating lameness and pain in the meniscal release model of osteoarthritis. Grapiprant given at 30 mg/kg was considered safe for at least a 14-day treatment period; however, serum protein levels decreased slightly.

Example 9—Effectiveness of Grapiprant for Controlling Pain and Inflammation in Feline Onychectomy (FCL-12-002)

This controlled, non-GLP, laboratory study used three treatment groups: Group 1 was dosed with 20-mg grapiprant-containing Formulation A34 tablets the night before (about 12 hours) and 30 minutes before surgery; Group 2 was the negative control dosed with empty gelatin capsules; and Group 3 was dosed with two 20-mg grapiprant-containing Formulation A34 tablets given 30 minutes before surgery.

Ten adult cats were in each group. The cats were acclimated for 7 days. Cats were divided into two sequences of 15 cats each to allow for surgeries over two days. The day of surgery was considered Day 0 for that sequence. One cat from each grapiprant-treated group was removed before surgical procedures were performed. On Day −1/0 for that sequence, all animals were administered with the appropriate test article before onychectomy. All animals received a dose of butorphanol before surgery. Following Day 2 procedures, all animals were transferred to an open feline colony. Study parameters of interest included statistical analysis of recovery, sedation, analgesia scores, and clinical pathology.

In summary, administering test article grapiprant was associated with decreased analgesia scores (reduced pain) without an apparent effect on sedation scores compared to the placebo control. Both groups of grapiprant treated animals had fewer pain interventions than placebo control. Group 1 treatment regimen was associated with fewer pain interventions when compared to Group 3. Thus, dosing the cats with grapiprant the night before surgery was more effective than providing the same total amount of grapiprant to the cats only 30 minutes before surgery.

Example 10—Evaluating Dose Linearity and Effect of Feeding in Cats (FPK-11-001)

Grapiprant was blended in a mixture of excipients as shown in Table 14 and administered orally by capsule to male and female cats. Animals were assigned to groups as shown in Table 15.

TABLE 14

Grapiprant formulation used in this study

| Ingredient | Component % (by weight) |
| --- | --- |
| Grapiprant | 45 |
| Lactose 200 mesh | 23 |
| Dicalcium phosphate dihydrate | 15 |
| Pregelantized starch | 5 |
| Microcrystalline cellulose | 6 |
| Povidone | 5 |
| Polaxamer 188 | 1 |

TABLE 15

Study groups.

| Group | Number of Animals (M/F) | Dose Level (mg/kg) | Fed/Fasted |
| --- | --- | --- | --- |
| 1 | 3/3 | 2 | Fed |
| 2 | 3/3 | 2 | Fasted |
| 3 | 3/3 | 6 | Fasted |
| 4 | 3/3 | 10 | Fasted |

The day of dosing was defined as Day 0. Following dosing, the animals were evaluated for clinical signs. Blood samples were collected prior to dosing and at 0.25, 0.5, 1, 2, 4, 8, 12, and 24-hours postdose. The blood samples were processed to serum and analyzed for grapiprant concentration. There were no test article-related clinical signs. The mean grapiprant pharmacokinetic results were as follow in Table 16.

TABLE 16

| Group | Dose (mg/kg) | Food | Sex | Cmax (ng/mL) | Tmax (hr) | $AUC_{last}$ (hr*ng/mL) | $AUC_{0-\infty}$ (hr*ng/mL) | $t_{1/2}$ (hr) |
| --- | --- | --- | --- | --- | --- | --- | --- | --- |
| 1 | 2 | Fed | Male | 407 | 1.65 | 1030 | 1220 | 3.12 |
| 1 | 2 | Fed | Female | 327 | 1.33 | 990 | 1070 | 2.4 |
| 2 | 2 | Fasted | Male | 1100 | 1.01 | 2290 | 1970 | 2.16 |
| 2 | 2 | Fasted | Female | 1630 | 1.01 | 2780 | 2850 | 1.47 |
| 3 | 6 | Fasted | Male | 2970 | 0.99 | 3650 | 3750 | 2.79 |
| 3 | 6 | Fasted | Female | 3110 | 1.17 | 6130 | 6350 | 4.98 |
| 4 | 10 | Fasted | Male | 4280 | 1.33 | 7430 | 7580 | 4.03 |
| 4 | 10 | Fasted | Female | 7130 | 0.73 | 10700 | 10900 | 4.19 |

There were no sex differences although $C_{max}$ and AUC values in females were higher than in males for fasted cats, $C_{max}$ and AUC were lower in females for fed cats. Following a single oral dose of 2 mg/kg grapiprant capsule to Group 1 fed cats, the mean $T_{max}$ was 1.33 to 1.65 hours. The mean terminal half-life was 2.40 to 3.12 hours. Mean $C_{max}$ was 327 to 407 ng/mL, and mean $AUC_{0-\infty}$ was 1070 to 1220 hr*ng/mL.

After a single oral dose of 2 mg/kg grapiprant capsule to Group 2 fasted cats, the mean $T_{max}$ was 1.01 hours. The mean terminal half-life was 1.47 to 2.16 hours. Mean $C_{max}$ was 1100 to 1630 ng/mL, and mean $AUC_{0-\infty}$ was 1970 to 2850 hr*ng/mL. Following an oral dose of grapiprant capsule at 2 mg/kg, $C_{max}$ and AUCs were significantly higher (p<0.05) in fasted cats than in fed cats for both males and females. However, $T_{max}$ and $t_{1/2}$ were not significantly different.

After a single oral dose of 6 mg/kg grapiprant capsule to Group 3 fasted cats, the mean $T_{max}$ was 0.99 to 1.17 hours. The mean terminal half-life was 2.79 to 4.98 hours. Mean $C_{max}$ was 2970 to 3110 ng/mL, and mean $AUC_{0-\infty}$ was 3750 to 6350 hr*ng/mL.

After a single oral dose of 10 mg/kg grapiprant capsule to Group 4 fasted cats, the mean $T_{max}$ was 0.728 to 1.33 hours. The mean terminal half-life was 4.03 to 4.19 hours. Mean $C_{max}$ was 4280 to 7130 ng/mL, and mean $AUC_{0-\infty}$ was 7580 to 10900 hr*ng/mL. Greater exposure occurred when animals were dosed in the fasted state than in the fed state, as evidenced by greater AUC and $C_{max}$ for the Group 2 (fasted) than for the Group 1 (fed) animals.

Exposure ($AUC_{0-\infty}$) across groups of fasted animals (Groups 2-4) was roughly dose-linear but less than dose-proportional. One-time grapiprant administration (orally, via capsule) to male and female cats at dose levels of 2 (fed and fasted), 6, and 10 mg/kg was well-tolerated with no test article-related clinical signs. Significantly (p<0.05) greater exposure occurred when animals were dosed in the fasted state than in the fed state, as evidenced by greater AUC and $C_{max}$ for the Group 2 (fasted) than for the Group 1 (fed) animals. Exposure ($AUC_{0-\infty}$) across groups of fasted animals (Groups 2-4) was roughly dose-linear but less than dose-proportional.

Example 11—Evaluation of Binding of Grapiprant to Cat Serum Proteins by Equilibrium Dialysis (FPK-12-002)

Grapiprant concentrations of 200 and 1000 ng/mL in cat serum were subjected to equilibrium dialysis using a Rapid Equilibrium Dialysis (RED) device. After dialysis, protein binding of grapiprant was high in cat serum. The percent bound of grapiprant in cat serum at 200 and 1000 ng/mL was 95% and 92%, respectively. Under these conditions, the change of grapiprant concentration had no significant effect on cat serum protein binding. The positive control compound warfarin (10 μM) was 99.2% bound to human plasma proteins.

Example 12—Pharmacokinetics Grapiprant in Cats (FPK-12-003)

This controlled, non-GLP, laboratory study included two treatment groups of six adult cats (three per sex) for a total of 12 study animals. All cats underwent an 8-day acclimation phase. On Day 0, fasted animals in Group 1 were orally-administered a 20-mg grapiprant-containing tablet (Formulation A34) while fasted animals in Group 2 were orally-administered a 20-mg grapiprant-containing tablet (Formulation A29). Blood samples were collected and processed to serum for pharmacokinetic (PK) analysis. Four hours post-dose, all cats were offered food. Following PK sample collections on Day 1, all animals were released to an open feline colony. The variable of interest for this study was the PK profile in serum. All animals were successfully dosed with the designated test article formulation of grapiprant. No abnormal general health was observed during the study. Grapiprant serum concentrations were successfully measured to determine the PK profile as shown in Table 17.

TABLE 17

| Formulation | Sex | Stat | Cmax (ng/mL) | Tmax (hr) | $AUC_{last}$ (hr*ng/mL) | $AUC_{last}$/Dose (hr*mg/mL) | $t_{1/2}$ (hr) |
|---|---|---|---|---|---|---|---|
| A29 | Male | Mean | 1029 | 1.3 | 4760 | 1182 | 1.7 |
|  |  | StDev | 818 | 0.3 | 3564 | 832 | 0.4 |
|  |  | CV % | 79.5 | 43.3 | 74.9 | — | 25.3 |
|  | Female | Mean | 4413 | 1.2 | 17089 | 2905 | 1.7 |
|  |  | StDev | 1535 | 0.8 | 4189 | 1253 | 0.3 |
|  |  | CV % | 34.8 | 65.5 | 24.5 | — | 19.3 |
| A34 | Male | Mean | 1664 | 0.8 | 5785 | 1419 | 5.0 |
|  |  | StDev | 1090 | 0.3 | 2534 | 638 | 2.9 |
|  |  | CV % | 65.5 | 34.6 | 43.8 | — | 57.9 |
|  | Female | Mean | 9630 | 1.2 | 29691 | 4606 | 2.5 |
|  |  | StDev | 4901 | 0.8 | 8780 | 968 | 0.7 |
|  |  | CV % | 50.9 | 65.5 | 29.6 | — | 27.7 |

In general, there were no abnormal general health observations during the study. Female cats demonstrated a greater systemic exposure than males for both the A29 and A34 formulations. Male cats demonstrated similar system exposure between the A29 and A34 formulations. Female cats receiving grapiprant in the A34 formulation demonstrated greater systemic grapiprant exposure than female cats administered the A29 formulation. All female cats received a greater mg/kg dose than those of male cats; however, when adjusted for dose administered (mg/kg), female cats continued to have a greater systemic grapiprant exposure than male cats.

Example 13—Pharmacokinetics of Grapiprant in Cats (FPK-13-004)

This controlled, non-GLP, laboratory study used three treatment groups: Group 1 was dosed with grapiprant at 2.5 mg/animal; Group 2 was dosed with grapiprant at 5 mg/animal; and Group 3 was dosed with grapiprant at 10 mg/animal. Each dose was administered once on Day 0. Blood samples were collected and processed to serum for pharmacokinetic (PK) analysis. Four hours post-dose, all cats were offered food. Following PK sample collections on Day 1, all animals were released to an open feline colony.

The mean pharmacokinetic parameters of grapiprant are presented in Table 18 below. Pharmacokinetic parameters were similar between males and females within each dose group, and therefore mean values were determined by combining data from all animals.

TABLE 18

Pharmacokinetic Data.

| Dose (mg) | Dosage (mg/kg) | $T_{max}$ (hr) | $C_{max}$ (ng/mL) | $C_{max}$/Dose (kg*ng/mL/mg) | $AUC_{last}$ (hr*ng/mL) | $AUC_{last}$/Dose (hr*ng/mL) | $t_{1/2}$ (hr) |
|---|---|---|---|---|---|---|---|
| 2.5 | 0.5 | 1.50 | 1060 | 2120 | 4190 | 8380 | 1.58 |
| 5 | 1 | 1.13 | 2690 | 2500 | 10300 | 9450 | 1.13 |
| 10 | 2 | 1.25 | 4430 | 2150 | 21200 | 10300 | 3.44 |

Mean $T_{max}$ values were similar among groups, ranging from 1.13 to 1.50 hours. Elimination half-life values were similar between the 0.5 and 1 mg/kg doses (1.58 and 1.13 hours, respectively) and increased slightly for the 2 mg/kg dose (3.44 hours). Increases in $C_{max}$ were about dose proportional, and increases in $AUC_{last}$ values were slightly greater than dose proportional. For a 4-fold increase in dose from 0.5 to 2 mg/kg, $C_{max}$ increased 4.18-fold, and $AUC_{last}$ values increased 5.06-fold. Overall, the data indicate that the 2 mg/kg dosage was the most effective in providing cats with grapiprant.

Example 14—Safety and Toxicokinetic Profiles of Grapiprant in Cats

The objective of this study was to evaluate the feline safety and toxicokinetic profiles of grapiprant. Twenty-four domestic shorthair cats were randomly assigned to receive placebo or 3, 9, or 15 mg/kg grapiprant in a capsule formulation (3 males and 3 females per group) once daily for 28 days. All cats received their assigned medications as per protocol. Food consumption and behavior were observed daily, bodyweight measured weekly, and clinical pathology analyses on blood run on Days −7, 14, and 25, and urinalysis run on Days −7, and 25. Serial blood samples for toxicokinetic analyses were obtained following the Day 0 and Day 27 doses. Full necropsies and histopathological evaluations were performed following humane euthanasia on Day 28.

Grapiprant was well tolerated, and no adverse effects were noted at daily doses up to 15 mg/kg for 28 days. All animals appeared normal throughout the study. Grapiprant caused no deaths or drug-related effects on body weight, food consumption, clinical pathology, organ weight, gross pathology, or histopathology.

Grapiprant rapidly reached peak serum concentrations and maintained substantial levels throughout the study. Grapiprant exposure varied with dose, but the 9 mg/kg and the 15 mg/kg groups showed similar mean $AUC_{last}$ values. By Day 27, maximum grapiprant serum concentrations ranged from 683 ng/mL to 4950 ng/mL, and these were reached by 1-4 hours after administration. Mean half-lives on Day 27 ranged from about 3 to about 14 hours, with a median value of about 5 to about 6 hours.

Grapiprant in a capsule formulation was well tolerated when given for 28 days at serum exposures up to 4950 ng/mL.

Example 15—Further Pharmacokinetic Study of Grapiprant in Dogs

The objective of this study was to determine and compare the pharmacokinetic parameters of grapiprant in beagle dogs after single oral administration of a flavored tablet formulation and a methylcellulose suspension formulation at nominal doses of 6 mg/kg and 50 mg/kg. For this study, sixteen beagle dogs, two per sex per dose, were divided into two groups based on the nominal doses of grapiprant, either 6 mg/kg in Groups 3AB or 50 mg/kg in Groups 4A/B. Each group was given the appropriate oral dose in a tablet or in a methylcellulose formulation, using the crossover design as shown below at Table 19, on study Days 0 and 15. Blood samples were collected and serum was prepared, frozen, and analyzed for concentration of grapiprant.

The vehicle was 0.5% methylcellulose (400 centipoise) in water. About half a volume of distilled water was heated to about 40-50° C. Methylcellulose was weighed to give a final concentration of 0.5% (w/v), and dissolved in the heated distilled water with stirring. The flask with the methylcellulose solution was cooled immediately. The remaining distilled water was added into the flask to adjust volume. The final solution was stirred for least 30 minutes.

To prepare 1.2-mg/mL and 10-mg/mL suspensions grapiprant in the vehicle, an appropriate amount of grapiprant was added to a calibrated beaker containing 0.5% aqueous methylcellulose, and mixed using a vortex. The suspension was homogenized using a Polytron™ mixer with attached antifoam bit. A stir bar was added to the beaker, and the suspension was stirred for about 5 minutes. The stir bar was removed temporarily to adjust the volume, and the suspension was stirred for another 5 minutes before it was transferred to a labeled amber dosing container or glass beaker wrapped with foil.

The dosing suspension was prepared fresh on each day of dosing. A vortex depth of between 75% and 100% of the depth of the container containing the 500-mg suspension was achieved on both dosing days. Stirring sufficient enough to create a vortex of this depth resulted in a homogenous mixture, as shown by all formulation samples having between 93% and 100% of the nominal concentration. Dose formulation samples were transported to the animal room before collection and were collected (while the formulations were being stirred) just before dosing the first animal of each group, and just before dosing the last animal of each group. These steps guard against the 500-mg suspension settling during transport from the formulation laboratory to the animal room.

TABLE 19

Group Assignment and Dose Levels.

| Group | No. of Animals | Type of Dosing | Day 0 | Day 15 |
|---|---|---|---|---|
| 3A | 2M/2F | Tablet/Suspension | 60-mg tablet | 60-mg suspension |
| 3B | 2M/2F | Suspension/Tablet | 60-mg suspension | 60-mg tablet |
| 4A | 2M/2F | Tablet/Suspension | Five 100-mg tablets | 500-mg suspension |
| 4B | 2M/2F | Suspension/Tablet | 500-mg suspension | Five 100-mg tablets |

The gavage tube was closely examined postdose after dosing of all animals on both days. No notable amounts of test article were observed in any gavage tube. There was no mortality. Slight increases in the incidence of fecal abnormalities were noted and are considered related to grapiprant exposure.

The $T_{max}$ on Day 0 at the 60-mg dose was 1.0 or 2.0 hours for the tablet and 1.0 hour for the suspension. The average $C_{max}$ for both sexes combined was 5,330 ng/mL for the 60-mg tablet and 4,050 ng/mL for the 60-mg suspension. The average $AUC_{last}$ for both sexes combined was 19,600 hr*ng/mL for the 60-mg tablet and 14,500 hr*ng/mL for the 60-mg suspension.

The $T_{max}$ on Day 0 at the 500-mg dose was 1.0, 2.0, or 4.0 hours for the tablet and 0.5, 1.0, or 2.0 hours for the suspension. The average $C_{max}$ for both sexes combined was 96,100 ng/mL for the 500-mg tablet and 76,800 ng/mL for the 500-mg suspension. The average $AUC_{last}$ for both sexes combined was 455,000 hr*ng/mL for the 500-mg tablet and 293,000 hr*ng/mL for the 500-mg suspension.

The $T_{max}$ on Day 15 at the 60-mg dose was 1.0 or 2.0 hours for the tablet and 1.0 hour for the suspension. The average $C_{max}$ for both sexes combined was 6,110 ng/mL for the 60-mg tablet and 3,810 ng/mL for the 60-mg suspension. The average $AUC_{last}$ for both sexes combined was 17,400 hr*ng/mL for the 60-mg tablet and 12,500 hr*ng/mL for the 60-mg suspension.

The $T_{max}$ on Day 15 at the 500-mg dose was 1.0 or 2.0 hours for the tablet and 1.0 hour for the suspension. The average $C_{max}$ for both sexes combined was 101,000 ng/mL for the 500-mg tablet and 74,200 ng/mL for the 500-mg suspension. The average $AUC_{last}$ for both sexes combined was 430,000 hr*ng/mL for the 500-mg tablet and 209,000 hr*ng/mL for the 500-mg suspension.

$T_{max}$, $C_{max}$, and $AUC_{last}$ were higher at the 500-mg dose than at the 60-mg dose. $C_{max}$ and $AUC_{last}$ values were similar for a given dose on Days 0 and 15. There were differences in pharmacokinetic parameters between the tablet and suspension at both doses, with exposure ($AUC_{last}$) greater in the tablet formulation versus the suspension formulation. ANOVA indicated that for the tablet versus the suspension formulations there was a significant difference ($p \leq 0.05$) for $C_{max}$ and $AUC_{last}$ at the 60-mg dose, and a significant difference ($p \leq 0.05$ or $p \leq 0.01$) for $T_{max}$ and $AUC_{last}$ at the 500-mg dose. Statistical differences occurred with and without the data from an animal that vomited in the first 11 minutes of dosing. Overall, the $AUC_{last}$ coefficients of variation of the 500-mg suspension were 53.7% (pharmacokinetic data from an animal with emesis excluded) on Day 0 and 28.7% on Day 15.

Thus, results showed greater exposure (AUC) with the tablet formulation compared to the suspension. The difference between AUCs for tablet and suspension was statistically significant at both 60 mg and 500 mg, both when animals with emesis were included and excluded from the analysis. The relative bioavailability ratio (tablet/suspension) for both dose levels, in both trials, was consistently greater than 100, which indicated that tablet bioavailability was greater than suspension bioavailability. The relative bioavailability ratio greater than 100 difference persisted irrespective of whether animals with emesis were included or excluded from the analysis.

What is claimed is:

1. A method for treating pain and inflammation in a cat or a dog, the method comprising administering to the cat or the dog an oral pharmaceutical composition comprising a therapeutically effective amount of grapiprant and one or more excipients;
   wherein the therapeutically effective amount of grapiprant is administered at a dosage rate of 2 mg per kilogram bodyweight of the cat or the dog once per day; and
   wherein the oral pharmaceutical composition is administered with or without food.

2. The method of claim 1, wherein the administering achieves a $C_{max}$ of grapiprant of 375 ng/ml to 10000 ng/mL at a Tax of 0.4 to 3.4 hours.

3. The method of claim 2, wherein the administering achieves a $C_{max}$ of grapiprant of 750 ng/mL to 4000 ng/mL.

4. The method of claim 3 wherein the administering achieves a $C_{max}$ of grapiprant of 1300 ng/mL to 4000 ng/mL.

5. The method of claim 2, wherein the administering achieves the $C_{max}$ of grapiprant at a $T_{max}$ of 0.7 to 1.7 hours.

6. The method of claim 3, wherein the administering achieves the $C_{max}$ of grapiprant at a $T_{max}$ of 0.5 to 1.0 hours.

7. The method of claim 1, wherein the pharmaceutical composition further comprises 1% to 30% flavorant (w/w of the total composition).

8. The method of claim 7, wherein the pharmaceutical composition comprises 5% to 15% flavorant (w/w of the total composition).

9. The method of claim 1, wherein the pharmaceutical composition is administered for 6 days to 9 months.

10. The method of claim 9, wherein the pharmaceutical composition is administered for 9 to 21 days.

11. The method of claim 10, wherein the pharmaceutical composition is administered for 12 to 14 days.

12. The method of claim 1, wherein the administering occurs from about 10 hours to about 18 hours before a surgery is performed on the cat or the dog.

13. The method of claim 1, wherein the pharmaceutical composition comprises sodium lauryl sulfate.

14. The method of claim 1, wherein the composition after administering causes no clinically significant adverse gastrointestinal event or changes in liver, kidney, and coagulation parameters in the cat or the dog.

* * * * *